US009663742B2

(12) United States Patent
Fujiwara et al.

(10) Patent No.: US 9,663,742 B2
(45) Date of Patent: May 30, 2017

(54) PRODUCTION METHOD FOR COMPLEX POLYESTER COMPOSITION, COMPLEX POLYESTER COMPOSITION, LUBRICANT COMPOSITION, AND LUBRICANT

(71) Applicant: FUJIFILM Corporation, Tokyo (JP)

(72) Inventors: Toshiki Fujiwara, Ashigarakami-gun (JP); Yuji Terada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/010,990

(22) Filed: Jan. 29, 2016

(65) Prior Publication Data

US 2016/0145526 A1    May 26, 2016

Related U.S. Application Data

(63) Continuation of application No. PCT/JP2014/070059, filed on Jul. 30, 2014.

(30) Foreign Application Priority Data

Jul. 31, 2013  (JP) .................................. 2013-159833

(51) Int. Cl.
*C07C 69/34* (2006.01)
*C07C 69/52* (2006.01)
(Continued)

(52) U.S. Cl.
CPC ............ *C10M 129/78* (2013.01); *C07C 67/08* (2013.01); *C07C 69/708* (2013.01); *C08G 63/12* (2013.01);
(Continued)

(58) Field of Classification Search
None
See application file for complete search history.

(56) References Cited

U.S. PATENT DOCUMENTS 5,364,956 A    11/1994  Matsumoto
7,119,056 B2   10/2006  Koch et al.
(Continued)

FOREIGN PATENT DOCUMENTS

JP    5-155809 A     6/1993
JP    2002-97482 A   4/2002
(Continued)

OTHER PUBLICATIONS

International Preliminary Report on Patentability (Forms PCT/IPEA/409 and PCT/IPEA/416), mailed Feb. 17, 2015, issued in PCT/JP2014/070059.
(Continued)

*Primary Examiner* — Vishal Vasisth
(74) *Attorney, Agent, or Firm* — Birch, Stewart, Kolasch & Birch, LLP

(57) ABSTRACT

A production method for a complex polyester composition includes obtaining a complex polyester composition by condensing polyhydric alcohol having three or more hydroxyl groups, a polycarboxylic acid having at least two carboxyl groups and carbon atoms of greater than or equal to 5, and monohydric alcohol having at least one oxyalkylene group in the absence of a solvent, wherein a component having a weight average molecular weight of less than or equal to 2000 in a GPC chart of the complex polyester composition is less than or equal to 43 area %.

15 Claims, 1 Drawing Sheet

(51) Int. Cl.
  *C10M 105/42* (2006.01)
  *C10M 129/78* (2006.01)
  *C08G 63/668* (2006.01)
  *C10M 177/00* (2006.01)
  *C07C 67/08* (2006.01)
  *C07C 69/708* (2006.01)
  *C08G 63/12* (2006.01)
  *C08G 63/127* (2006.01)
  *C08G 63/16* (2006.01)
  *C08G 63/78* (2006.01)
  *C10M 101/02* (2006.01)
  *C10M 105/00* (2006.01)
  *C10M 169/04* (2006.01)

(52) U.S. Cl.
  CPC ........... *C08G 63/127* (2013.01); *C08G 63/16* (2013.01); *C08G 63/668* (2013.01); *C08G 63/78* (2013.01); *C10M 101/02* (2013.01); *C10M 105/00* (2013.01); *C10M 105/42* (2013.01); *C10M 169/04* (2013.01); *C10M 177/00* (2013.01); *C10M 2207/30* (2013.01); *C10M 2207/301* (2013.01); *C10N 2230/06* (2013.01); *C10N 2230/64* (2013.01); *C10N 2240/02* (2013.01); *C10N 2240/08* (2013.01); *C10N 2240/10* (2013.01); *C10N 2240/12* (2013.01); *C10N 2240/14* (2013.01); *C10N 2240/204* (2013.01); *C10N 2240/30* (2013.01); *C10N 2240/40* (2013.01); *C10N 2240/58* (2013.01); *C10N 2250/10* (2013.01); *C10N 2270/00* (2013.01)

(56) References Cited

U.S. PATENT DOCUMENTS

2005/0101667 A1    5/2005  Koch et al.
2012/0184474 A1*   7/2012  Kawata ................. C07C 67/08
                                                        508/497

FOREIGN PATENT DOCUMENTS

| JP | 2004-507597 A | 3/2004 |
| JP | 2005-154726 A | 6/2005 |
| JP | 2005-213377 A | 8/2005 |
| JP | 2005-232434 A | 9/2005 |
| JP | 2005-232470 A | 9/2005 |
| JP | 2011-89106 A  | 5/2011 |

OTHER PUBLICATIONS

International Search Report, mailed Oct. 14, 2014, issued in PCT/JP2014/070059.
Written Opinion of the International Searching Authority, mailed Oct. 14, 2014, issued in PCT/JP2014/070059.
English translation of the International Preliminary Report on Patentability (Forms PCT/IB/338 and PCT/IPEA/409), dated Feb. 4, 2016, for International Application No. PCT/JP2014/070059.
Extended European Search Report, dated Apr. 26, 2016, for corresponding European Application No. 14831298.6
Chinese Office Action for Application No. 201480040049.8, dated Jan. 5, 2017, with English language machine translation.

* cited by examiner

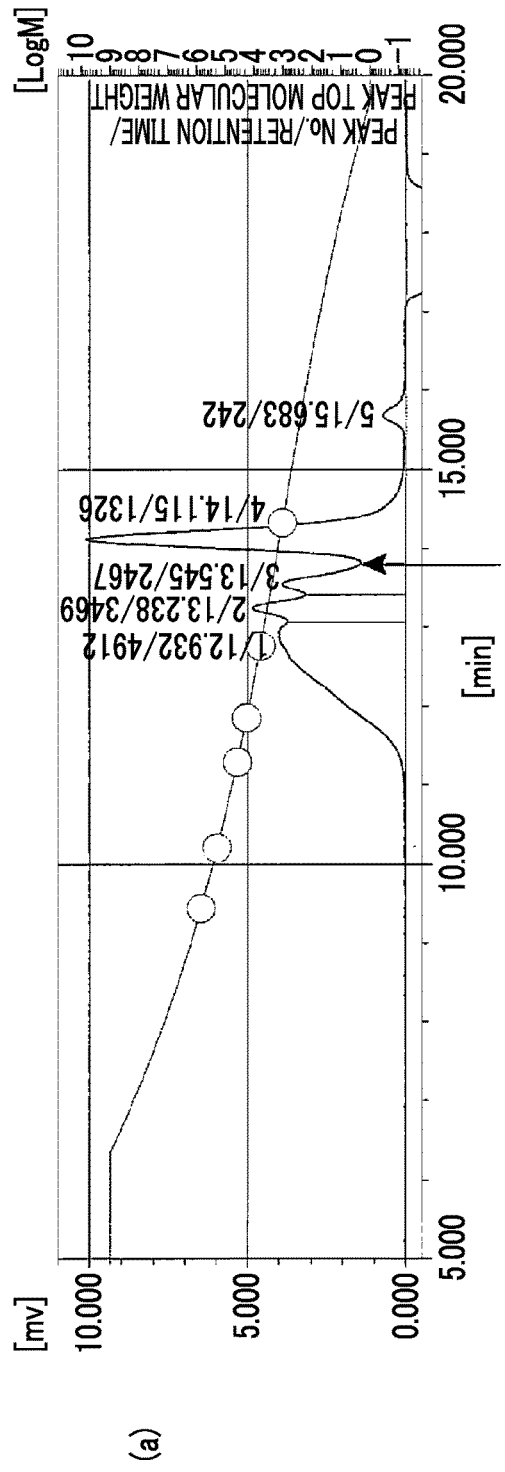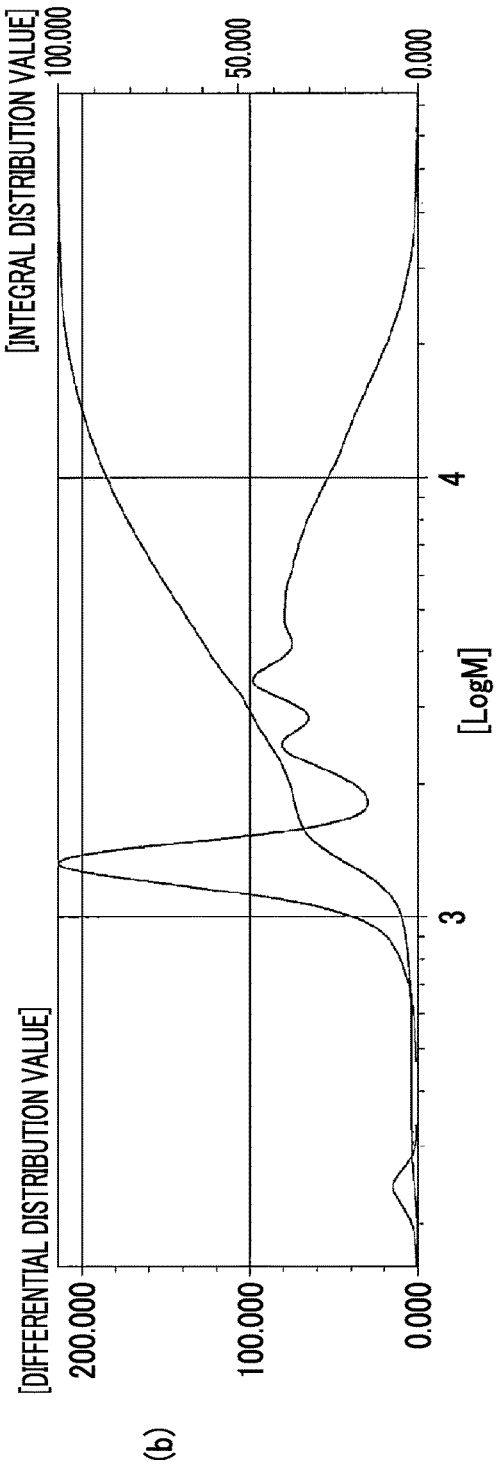

PRODUCTION METHOD FOR COMPLEX POLYESTER COMPOSITION, COMPLEX POLYESTER COMPOSITION, LUBRICANT COMPOSITION, AND LUBRICANT

CROSS-REFERENCE TO RELATED APPLICATIONS

This application is a Continuation of PCT International Application No. PCT/JP2014/070059, filed on Jul. 30, 2014, which claims priority under 35 U.S.C. Section 119(a) to Japanese Patent Application No. 2013-159833 filed on Jul. 31, 2013. Each of the above applications is hereby expressly incorporated by reference, in its entirety, into the present application.

BACKGROUND OF THE INVENTION

1. Field of the Invention

The present invention relates to a production method for a complex polyester composition. Specifically, the present invention relates to a production method for polyester in which specific polyester is condensed in the absence of a solvent, and a complex polyester composition of which a specific component having an area of less than or equal to a certain value in a GPC chart is produced.

2. Description of the Related Art

In general, a lubricant contains base oil and various additives. Examples of the base oil include mineral oil obtained from crude oil, ester-based oil which is chemically synthesized, fluorine oil, polyalphaolefin-based oil, and the like. Among them, the ester-based oil is preferably used in a jet plane, automobile engine oil, grease, and the like from the viewpoints of a low fluid point, a high viscosity index, a high flash point, excellent lubrication performance, biodegradability, and the like.

Various esters such as monoester obtained from a reaction between an aliphatic monocarboxylic acid and monohydric alcohol; diester obtained from a reaction between an aliphatic dibasic acid and monohydric alcohol; ester obtained from a reaction between polyhydric alcohol and an aliphatic carboxylic acid; and complex ester obtained from a reaction between polyol, a polybasic acid, and an aliphatic monocarboxylic acid, have been disclosed as the ester-based oil (JP2002-097482A, JP2005-154726A, JP2005-232434A, JP2005-213377A, and JP2005-232470A).

Recently, the lubricant has been required to have high lubrication performance according to diversification and advancement of the industrial field. For this reason, development of polyester having excellent lubrication performance has progressed. For example, in JP2011-89106A, a polyester composition which is obtained by a reaction between polyhydric alcohol, a polycarboxylic acid, and monohydric alcohol having an oxyalkylene group is disclosed. Here, a condensation reaction of the polyester composition is performed in the presence of a solvent.

SUMMARY OF THE INVENTION

However, according to the studies of the present inventors, it has been obvious that in the polyester composition of the related art, a large amount of light component having a weight average molecular weight of less than or equal to 2000 is contained, and thus the lubrication performance of the lubricant containing the polyester composition decreases.

In addition, the condensation reaction of the polyester composition of the related art is performed in the presence of a solvent, and thus when the polyester composition is mass produced, a load on an environment increases, and mass productivity deteriorates.

Therefore, in order to solve such problems of the related art and to provide a lubricant having excellent lubrication performance, the present inventors have carried out research. Further, in order to produce a polyester composition having a small load on an environment and mass productivity, the present inventors have carried out research.

As a result of intensive studies for attaining the objects described above, the present inventors have found that lubrication performance becomes excellent by obtaining a complex polyester composition by condensing polyhydric alcohol, a polycarboxylic acid having at least two carboxyl groups having carbon atoms of greater than or equal to 5, and monohydric alcohol having at least one oxyalkylene group in the absence of a solvent, in which a component having a weight average molecular weight of less than or equal to 2000 in a GPC chart of the complex polyester composition is less than or equal to 43 area %. Further, the present inventors have found that it is possible to mass produce the complex polyester composition while reducing a load on an environment by using such a production method, and have completed the present invention.

Specifically, the present invention has the following configurations.

[1] A production method for a complex polyester composition including a step of obtaining a complex polyester composition by condensing polyhydric alcohol, a polycarboxylic acid having at least two carboxyl groups and carbon atoms of greater than or equal to 5, and monohydric alcohol having at least one oxyalkylene group in the absence of a solvent, in which a component having a weight average molecular weight of less than or equal to 2000 in a GPC chart of the complex polyester composition is less than or equal to 43 area %.

[2] The production method for a complex polyester composition according to [1], in which the polyhydric alcohol has three or more hydroxyl groups.

[3] The production method for a complex polyester composition according to [1] or [2], in which the polyhydric alcohol is selected from pentaerythritol, trimethylol propane, glycerin, and dipentaerythritol.

[4] The production method for a complex polyester composition according to any one of [1] to [3], in which the number of carbon atoms of the monohydric alcohol is greater than or equal to 6.

[5] The production method for a complex polyester composition according to any one of [1] to [4], in which the monohydric alcohol is denoted by General Formula (1) described below.

General Formula (1)

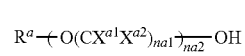

In General Formula (1), $R^a$ represents an alkyl group which may have a substituent group, a cycloalkyl group which may have a substituent group, an alkenyl group which may have a substituent group, an aryl group which may have a substituent group, or a heteroaryl group which may have a substituent group, and $X^{a1}$ and $X^{a2}$ each independently represent a hydrogen atom, a halogen atom, or an alkyl group. In addition, na1 represents an integer of 2 to 4, and na2 represents an integer of 1 to 12.

[6] The production method for a complex polyester composition according to any one of [1] to [5], in which the number of carbon atoms of the polycarboxylic acid is greater than or equal to 10.

[7] The production method for a complex polyester composition according to any one of [1] to [6], in which the number of carbon atoms of the polycarboxylic acid is 24 to 48.

[8] The production method for a complex polyester composition according to any one of [1] to [7], in which the polycarboxylic acid is a dimer acid or a trimer acid.

[9] The production method for a complex polyester composition according to any one of [1] to [8], in which in the step of obtaining the complex polyester composition, the polyhydric alcohol, the polycarboxylic acid, and the monohydric alcohol are condensed by being mixed such that an equivalence ratio of the polycarboxylic acid with respect to the polyhydric alcohol is 1 to 4, and an equivalence ratio of the monohydric alcohol with respect to the polyhydric alcohol is 0.5 to 5.

[10] The production method for a complex polyester composition according to any one of [1] to [9], in which in the step of obtaining the complex polyester composition, the polyhydric alcohol, the polycarboxylic acid, and the monohydric alcohol are condensed by being mixed such that an equivalence ratio of the polycarboxylic acid with respect to the polyhydric alcohol is 2.2 to 4, and an equivalence ratio of the monohydric alcohol with respect to the polyhydric alcohol is 2.5 to 5.

[11] The production method for a complex polyester composition according to any one of [1] to [10], in which the component having a weight average molecular weight of less than or equal to 2000 in a GPC chart is an ester component denoted by General Formula (2) described below.

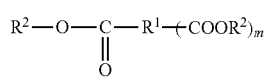

General Formula (2)

In General Formula (2), $R^1$ represents a (m+1)-valent or more chain or cyclic aliphatic linking group or an aromatic linking group, and $R^2$ represents a group having an oxyalkylene structure. In addition, m represents an integer of 1 to 3.

[12] A complex polyester composition produced by the production method according to any one of [1] to [11].

[13] A lubricant composition containing the complex polyester composition according to [12], and one type or two or more types of additives selected from an abrasion preventing agent, a viscosity index improver, an antioxidant, a cleaning agent, a dispersant, a fluidizing agent, a curing agent, a corrosion preventing agent, a seal compatible agent, a defoaming agent, a rust preventing agent, a friction adjuster, and a thickener.

[14] A lubricant composition containing at least the complex polyester composition according to [12] or the lubricant composition according to [13], and one type or two or more types of mediums selected from mineral oil, a fatty oil compound, polyolefin oil, silicone oil, perfluoropolyether oil, diphenyl ether oil, aromatic ester oil, aliphatic monoester oil, aliphatic diester oil, and polyol ester lubricating oil.

[15] A lubricant containing the complex polyester composition according to [12] or the lubricant composition according to [13] or [14].

[16] The lubricant according to [15], in which the lubricant is used as lubricating oil for grease, a releasing agent, engine oil for an internal combustion engine, oil for metal working (machining), oil for a bearing, fuel for a combustion engine, vehicle engine oil, gear oil, operating oil for an automobile, lubricating oil for a vessel and an aircraft, machine oil, turbine oil, hydraulic operating oil, compressor and vacuum pump oil, freezer oil, lubricating oil for metal working, a lubricant for magnetic recording medium, a lubricant for a micro machine, a lubricant for an artificial bone, shock absorber oil, or rolling oil.

According to the present invention, it is possible to obtain a complex polyester composition which is able to exhibit excellent lubrication performance. Further, by using a production method of the present invention, it is possible to mass produce a complex polyester composition while reducing a load on an environment.

BRIEF DESCRIPTION OF THE DRAWINGS

FIG. 1 is a GPC chart of a complex polyester composition according to this embodiment.

DESCRIPTION OF THE PREFERRED EMBODIMENTS

Hereinafter, the present invention will be described in detail. The following description of configuration requirements are based on representative embodiments or specific examples, but the present invention is not limited to the embodiments. Furthermore, herein, "to" indicates a range including the numerical values before and after "to" as the lower limit value and the upper limit value.

The present invention relates to a production method for a complex polyester composition including a step of obtaining a complex polyester composition by condensing polyhydric alcohol, a polycarboxylic acid having at least two carboxyl groups and carbon atoms of greater than or equal to 5, and monohydric alcohol having at least one oxyalkylene group in the absence of a solvent, in which a component having a weight average molecular weight of less than or equal to 2000 in a GPC chart of the complex polyester composition is less than or equal to 43 area %. In the present invention, such specific polyester is condensed in the absence of a solvent, and the component having a weight average molecular weight of less than or equal to 2000 in the GPC chart of the complex polyester composition is less than or equal to a certain area %, and thus it is possible to obtain a complex polyester composition having excellent lubrication performance. Further, the complex polyester composition obtained in the present invention is condensed in the absence of a solvent, and thus the complex polyester composition has a small load on an environment and mass productivity.

(Complex Polyester Composition)

The complex polyester composition is obtained by condensing polyhydric alcohol having at least two hydroxyl groups, a polycarboxylic acid having at least two carboxyl groups and carbon atoms of greater than or equal to 5, and monohydric alcohol having at least one oxyalkylene group. In addition, the component having a weight average molecular weight of less than or equal to 2000 in the gel permeation chromatography (GPC) chart of the complex polyester composition is less than or equal to 43 area %. The component having a weight average molecular weight of less than or equal to 2000 in the GPC chart of the complex polyester composition may be less than or equal to 43 area %, is preferably less than or equal to 40 area %, and is more preferably less than or equal to 38 area %. Furthermore, the component having a weight average molecular weight of less than or equal to 2000 in the GPC chart of the complex polyester composition is preferably greater than or equal to 25 area %, and is more preferably greater than or equal to 30 area %.

In FIG. 1, the GPC chart of the complex polyester composition obtained in the present invention is illustrated. In FIG. 1(a), a vertical axis on a right side of a graph indicates peak intensity. In addition, a horizontal axis of the graph indicates elution time. Furthermore, in FIG. 1, a portion indicated by a solid arrow corresponds to a weight average molecular weight of 1820, and the area of a region under the portion is obtained in consideration of a measurement error of approximately 10% and is set to a light component having a weight average molecular weight of less than or equal to 2000. The existing amount of the light component having a weight average molecular weight of less than or equal to 2000 is able to be indicated by area %, and in the present invention, the component having a weight average molecular weight of less than or equal to 2000 is in the range described above.

In the chart of FIG. 1(a), an arbitrary mark "○" indicates a weight average molecular weight (Mw) of a sample of TOSOH TSK standard POLYSTYRE as a reference. Furthermore, the weight average molecular weight of each of the marks "○" is as follows.

F-80(TS-201) 706000
F-20(TS-140) 190000
F-4(TS-202) 37900
F-2(TS-504) 18100
A-5000(TS-503) 5970
A-1000(TS-501) 1050

In the chart of FIG. 1(b), a horizontal axis of a graph indicates a weight average molecular weight (Log). That is, Log M=3 indicates a weight average molecular weight of 1000, and Log M=4 indicates a weight average molecular weight of 10000. Accordingly, a value corresponding to the peak minimum value between peaks 3 and 4 is Log M=3.26, and thus corresponds to a weight average molecular weight of 1820. In addition, each vertical axis indicates a differential distribution value and an integral distribution value of the peak.

A "HLC-8220GPC (manufactured by TOSOH CORPORATION) device" and the like are able to be used as a gel permeation chromatography (GPC) device. Three columns of "TSKgel, SuperHZM-H (manufactured by TOSOH CORPORATION, 4.6 mmID×15 cm)", "TSKgel, SuperHZ4000 (manufactured by TOSOH CORPORATION, 4.6 mmID×15 cm)", and "TSKgel, SuperHZ2000 (manufactured by TOSOH CORPORATION, 4.6 mmID×15 cm)" are able to be used as a column, and "TSKguardcolumn, SuperHZ-H (manufactured by TOSOH CORPORATION, 4.6 mmID×15 cm)" is able to be used as a guard column.

For example, the following conditions are able to be adopted as the conditions of GPC.

Eluant THF Stabilizer-Containing Liquid
Method THF8220
Flow Rate 0.35 ml/min
Measurement Temperature 40° C. (Column, Inlet, R.I.)
Analysis Time 20 minutes
Collection Conditions Sampling Pitch of 100 msec
Standard Concentration 0.1%
Sample Concentration 0.1% (5 mg+5 ml (Eluant) (Filtration with Filter of 0.45 μm)
Sample Injection Amount 10 μl In addition, a calibration curve, for example, is able to be prepared from the following six samples of "TSK standard POLYSTYRENE" manufactured by TOSOH CORPORATION.

$7.06 \times 10^5$ F-80(TS-201)
$1.90 \times 10^5$ F-20(TS-140)
$3.79 \times 10^4$ F-4(TS-202)
$1.81 \times 10^4$ F-2(TS-504)
$5.97 \times 10^3$ A-5000(TS-503)
$1.05 \times 10^3$ A-1000(TS-501)

In the present invention, in order to set the component having a weight average molecular weight of less than or equal to 2000 in the GPC chart of the complex polyester composition to be less than or equal to 43 area %, it is important that polyhydric alcohol having at least two hydroxyl groups, a polycarboxylic acid having at least two carboxyl groups and carbon atoms of greater than or equal to 5, and monohydric alcohol having at least one oxyalkylene group are condensed in the absence of a solvent. In addition, a reaction temperature at the time of performing the condensation is 120° C. to 250° C., is preferably 130° C. to 230° C., is more preferably 130° C. to 220° C., and is particularly preferably 140° C. to 220° C.

<Polyhydric Alcohol>

The polyhydric alcohol used in the condensation of the polyester is a compound having at least two hydroxyl groups. The polyhydric alcohol is denoted by $R(OH)_n$. R represents an n-valent aliphatic group, an n-valent aliphatic ring group, or an n-valent aromatic ring group, and in carbon atoms of R, one or more carbon atoms which are not adjacent to each other may be substituted with an oxygen atom. The number of hydroxyl groups contained in one molecule of the polyhydric alcohol is preferably 2 to 6, is more preferably 2 to 4, and is even more preferably 3 or 4. That is, it is preferable that the polyhydric alcohol is triol or tetraol.

Any one type of polyhydric alcohol of dihydric to tetrahydric alcohol may be used as the polyhydric alcohol used in the present invention, or a plurality types thereof may be used as the polyhydric alcohol used in the present invention. For example, a mixture of polyhydric alcohol of dihydric alcohol and polyhydric alcohol of trihydric alcohol may be used, a mixture of polyhydric alcohol of dihydric alcohol, polyhydric alcohol of trihydric alcohol, and polyhydric alcohol of tetrahydric alcohol may be used, or a mixture of polyhydric alcohol of trihydric alcohol and polyhydric alcohol of tetrahydric alcohol may be used. Furthermore, when the polyhydric alcohol contains the bivalent polyhydric alcohol, a content ratio of the bivalent polyhydric alcohol is preferably less than or equal to 40 mass %, is more preferably less than or equal to 30 mass %, and is even more preferably less than or equal to 20 mass %, with respect to the total mass of the polyhydric alcohol.

R is an n-valent aliphatic group which preferably has 2 to 20 carbon atoms, more preferably has 2 to 15 carbon atoms, even more preferably has 2 to 10 carbon atoms, still more preferably has 2 to 7 carbon atoms, and particularly preferably has 3 to 6 carbon atoms. However, the present invention is not limited to this range, and it may be preferable that the number of carbon atoms increases according to the application.

It is more preferable that R represents a group denoted by $C_xH_{2x+2-n}$ (x represents a numerical value of 2 to 20) or $C_xH_{2X+2-n}O_m$ (x represents a numerical value of 2 to 20, m represents a numerical value satisfying m<x, and m≤x/2 is preferable).

Examples of the polyhydric alcohol which is able to be used in the present invention are able to include the following compounds. Examples of the polyhydric alcohol which is able to be used in the present invention include diol such as ethylene glycol, propylene glycol, 1,4-butane diol, 1,3-butane diol, 1,6-hexane diol, 1,4-dimethylol cyclohexane, and neopentyl glycol; triol such as trimethylol methane, trimethylol ethane, trimethylol propane, trimethylol butane, and glycerin; tetraol such as tetramethylol propane, maltiol such as dipentaerythritol and tripentaerythritol; sugar alcohol such as xylitol, sorbitol, mannitol, erythritol, maltitol, isomalt, arabinitol, ribitol, iditol, volemitol, and perseitol; sugar such as glucose; and the like. Among them, the neopentyl glycol, the trimethylol ethane, the trimethylol propane, the trimethylol butane, the glycerin, the pentaerythritol, the dipentaerythritol, and the xylitol are preferable; polyhydric alcohol having three of more hydroxyl groups, such as the trimethylol propane, the trimethylol butane, the glycerin, the pentaerythritol, and the dipentaerythritol is more preferable; the trimethylol propane, the glycerin, the pentaerythritol, the dipentaerythritol, and the like are even more preferable; and the pentaerythritol and the trimethylol propane are particularly preferable. It is not necessary that these polyhydric alcohols are high-purity products, and a so-called industrial grade is preferably used. For example, the industrial grade of pentaerythritol is formed of mono-pentaerythritol of approximately 88%, di-pentaerythritol of 10%, and tri-pentaerythritol of 1% to 2%, and in the present invention, the industrial grade of the pentaerythritol or the like is able to be used as the polyhydric alcohol.

Hereinafter, specific examples of the polyhydric alcohol which is able to be used in the present invention will be described, but the present invention is not limited thereto.

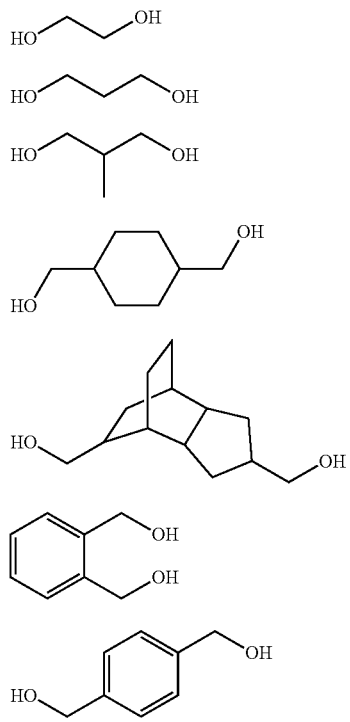

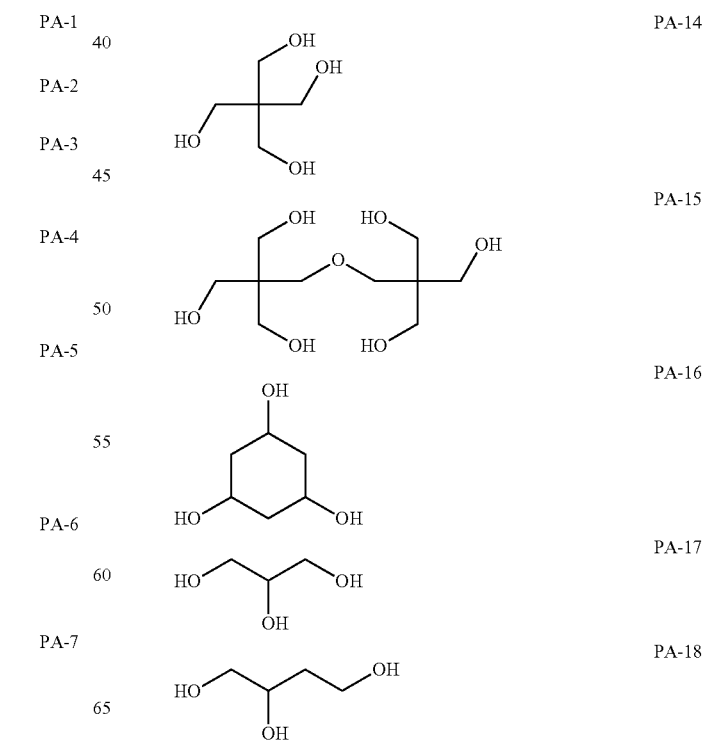

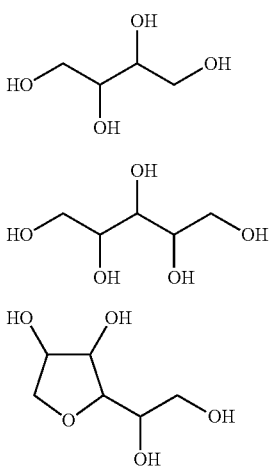

PA-19

PA-20

PA-21

<Polycarboxylic Acid>

The polycarboxylic acid used in the condensation of the polyester is a compound having carbon atoms of greater than or equal to 5 and at least two carboxyl groups. The number of carboxyl groups contained in one molecule is preferably 2 to 4, is more preferably 2 or 3. In addition, it is preferable that the polycarboxylic acid is a dimer acid or a trimer acid.

Any one type of bivalent to tetravalent polycarboxylic acid may be used as the polycarboxylic acid used in the present invention, or a plurality types thereof may be used as the polycarboxylic acid used in the present invention. For example, a mixture of a bivalent carboxylic acid and a trivalent carboxylic acid may be used, a mixture of a bivalent carboxylic acid, a trivalent carboxylic acid, and a tetravalent carboxylic acid may be used, or a mixture of a trivalent carboxylic acid and a tetravalent carboxylic acid may be used.

The number of carbon atoms of the polycarboxylic acid may be greater than or equal to 5, is preferably greater than or equal to 8, is more preferably greater than or equal to 10, is even more preferably greater than or equal to 16, and is still more preferably greater than or equal to 24. In addition, the number of carbon atoms of the polycarboxylic acid is preferably less than or equal to 66, is more preferably less than or equal to 60, and is even more preferably less than or equal to 48. Among them, it is particularly preferable that the number of carbon atoms of the polycarboxylic acid is 24 to 48. Furthermore, in the present invention, the number of carbon atoms of the polycarboxylic acid indicates the number of carbon atoms including carbon atoms configuring the carboxyl group. By setting the number of carbon atoms of the polycarboxylic acid to be in the range described above, it is possible to further increase the lubrication performance of the complex polyester composition.

The carboxyl groups in the molecules are connected by bivalent or more chain or cyclic aliphatic hydrocarbon or aromatic hydrocarbon. In carbon atoms of the aliphatic hydrocarbon linking group or the aromatic hydrocarbon linking group, one or more carbon atoms which are not adjacent to each other may be substituted with and oxygen atom. Among them, in the present invention, it is preferable that a group connecting the carboxyl groups in the molecules is aliphatic hydrocarbon having 20 to 46 carbon atoms.

Examples of the polycarboxylic acid which is able to be used in the present invention are able to include a terephthalic acid, a phthalic acid, a malonic acid, a succinic acid, a glutaric acid, an adipic acid, a suberic acid, an azelaic acid, a sebacic acid, a dodecanedioic acid, a trimellitic acid, a dimer acid and a hydrogenated body of the dimer acid, a trimer acid, and the like. Among them, it is preferable that the dimer acid and the hydrogenated body of the dimer acid, and the trimer acid are used.

Here, the dimer acid indicates an aliphatic dicarboxylic acid or an alicyclic dicarboxylic acid (in general, a trimer, a monomer, and the like are contained in several mol % in addition to a dimer which is the majority of the contents) which is generated by dimerizing an unsaturated fatty acid (in general, an unsaturated fatty acid having 18 carbon atoms) by polymerization, Diels-Alder reaction, or the like, and among them, an aliphatic dicarboxylic acid or an alicyclic dicarboxylic acid containing a trimer as a main component is defined as the trimer acid.

In specific examples of the dimer acid or the trimer acid, Tsunodymes (Registered Trademark) 205, 216, 228, and 395 manufactured by TSUNO CO., LTD. are exemplified as the dimer acid, and Tsunodyme 345 or the like is exemplified as the trimer acid. In addition, products manufactured by BASF SE or Croda International Plc. may be used.

Hereinafter, specific examples of the polycarboxylic acid which is able to be used in the present invention will be described, but the present invention is not limited thereto.

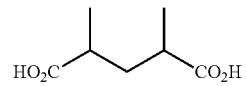

CA-1

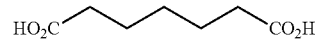

CA-2

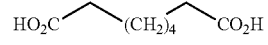

CA-3

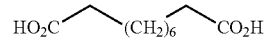

CA-4

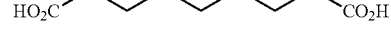

CA-5

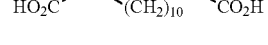

CA-6

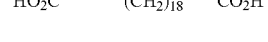

CA-7

$C_{34}H_{62}(COOH)_2$

Dimer Acid

CA-8

$C_{51}H_{93}(COOH)_3$

Trimer Acid

CA-9

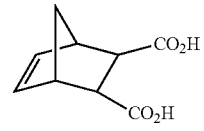

CA-10

CA-11

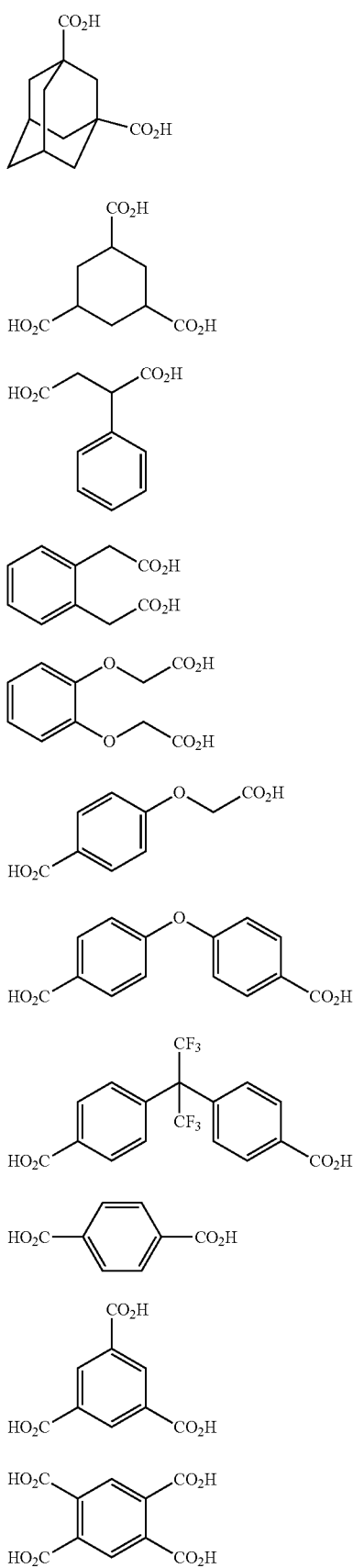

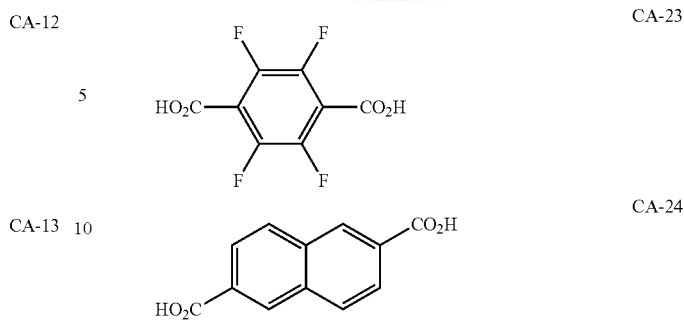

In the present invention, an anhydride of the polycarboxylic acid is able to be used instead of the polycarboxylic acid. The anhydride of the polycarboxylic acid is obtained by performing dehydration condensation with respect to two COOH groups of the polycarboxylic acid in the molecules or between the molecules. A preferred aspect thereof is as described above. Examples of the anhydride include a succinic acid anhydride, a glutaric acid anhydride, an adipic acid anhydride, a maleic acid anhydride, a phthalic acid anhydride, a nadic acid anhydride, a methyl nadic acid anhydride, a hexahydrophthalic acid anhydride, and an anhydride of mixed polybasic acids.

<Monohydric Alcohol>

The monohydric alcohol used in the condensation of the polyester is a compound having one hydroxyl group in one molecule, and is monohydric alcohol having at least one oxyalkylene group. The monohydric alcohol is denoted by R(OH). R represents a monovalent aliphatic group, a monovalent aliphatic ring group, or a monovalent aromatic ring group having an oxyalkylene structure. The number of carbon atoms of R is preferably greater than or equal to 6, is more preferably greater than or equal to 8, and is even more preferably greater than or equal to 10. By setting the number of carbon atoms of the monohydric alcohol to be in the range described above, it is possible to suppress volatilization of the monohydric alcohol at the time of performing a condensation reaction, and it is possible to efficiently perform the condensation reaction of the polyester.

The monohydric alcohol used in the present invention has at least one oxyalkylene group. The oxyalkylene group indicates a structure in which an oxygen atom is introduced into an alkylene chain. The alkylene chain may be a straight chain, a branched chain, or a cyclic chain. In addition, the number of carbon atoms of the alkylene chain is preferably 1 to 10, is more preferably 2 to 8, and is even more preferably 2 to 4. In addition, the number of oxygen atoms to be introduced is preferably 1 to 10, and is more preferably 1 to 6, and is even more preferably 1 to 4.

It is preferable that the monohydric alcohol used in the present invention is denoted by General Formula (1) described below.

General Formula (1)

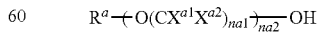

Here, in General Formula (1), $R^a$ represents an alkyl group which may have a substituent group, a cycloalkyl group which may have a substituent group, an alkenyl group which may have a substituent group, an aryl group which may have a substituent group, or a heteroaryl group which may have a substituent group, and $X^{a1}$ and $X^{a2}$ each independently represent a hydrogen atom, a halogen atom, or an alkyl group. In addition, na1 represents an integer of 2 to 4, and na1 represents an integer of 1 to 12.

In an alkyl group portion of the alkyl group represented by $R^a$ which may have a substituent group, the number of carbon atoms is preferably 3 to 17, is more preferably 4 to 13, and is even more preferably 5 to 9. The alkyl group represented by $R^a$ may be a straight-chain alkyl group or a branched alkyl group. In addition, $R^a$ may be a cycloalkyl group.

In an alkenyl group portion of the alkenyl group represented by $R^a$ which may have a substituent group, the number of carbon atoms is preferably 3 to 17, is more preferably 4 to 13, and is even more preferably 5 to 9. The alkenyl group represented by $R^a$ may be a straight-chain alkyl group, a branched alkyl group, or a cyclic alkyl group.

In an aryl group portion of the aryl group or the heteroaryl group represented by $R^a$ which may have a substituent group, the number of carbon atoms is preferably 6 to 17, and is more preferably 6 to 12. Examples of the aryl group represented by $R^a$ are able to include a phenyl group, a naphthyl group, and the like, and among them, the phenyl group is particularly preferable. In addition, an imidazolyl group, a pyridyl group, a quinolyl group, a furyl group, a thienyl group, a benzoxazolyl group, an indolyl group, a benzimidazolyl group, a benzothiazolyl group, a carbazolyl group, and an azepinyl group are able to be exemplified as the heteroaryl group represented by $R^a$. An oxygen atom, a sulfur atom, and a nitrogen atom are preferable as a hetero atom contained in the heteroaryl group, and among them, the oxygen atom is preferable.

Among them, in General Formula (1), it is preferable that $R^a$ is the alkyl group which may have a substituent group. Here, the alkyl group may be an alkyl group having a branch. In addition, it is more preferable that $X^{a1}$ and $X^{a2}$ each independently is a hydrogen atom or an alkyl group.

In General Formula (1), na1 is preferably an integer of 2 or 3, and is more preferably an integer of 2. In addition, na1 is preferably an integer of 1 to 8, is more preferably an integer of 1 to 6, and is particularly preferably an integer of 1 to 3.

The number of carbon atoms of the monohydric alcohol denoted by General Formula (1) is preferably greater than or equal to 6, is more preferably greater than or equal to 8, and is even more preferably greater than or equal to 10. By using such monohydric alcohol, it is possible to suppress the volatilization of the monohydric alcohol at the time of performing the condensation reaction, and it is possible to efficiently perform the condensation reaction of the polyester.

Examples of the substituent group which is able be included in $R^a$ include a substituted or unsubstituted alkyl group having 1 to 50 carbon atoms (for example, methyl, ethyl, straight-chain or branched-chain propyl, straight-chain or branched-chain butyl, straight-chain or branched-chain pentyl, straight-chain or branched-chain hexyl, straight-chain or branched-chain heptyl, straight-chain or branched-chain octyl, straight-chain or branched-chain nonyl, straight-chain or branched-chain decyl, straight-chain or branched-chain undecyl, straight-chain or branched-chain dodecyl, straight-chain or branched-chain tridecyl, straight-chain or branched-chain tetradecyl, straight-chain or branched-chain pentadecyl, straight-chain or branched-chain hexadecyl, straight-chain or branched-chain heptadecyl, straight-chain or branched-chain octadecyl, straight-chain or branched-chain nonadecyl, straight-chain or branched-chain eicosyl, straight-chain or branched-chain heneicosyl, straight-chain or branched-chain docosyl, straight-chain or branched-chain tricosyl, or straight-chain or branched-chain tetracosyl); an alkenyl group having 2 to 35 carbon atoms (for example, propenyl, butenyl, pentenyl, hexenyl, heptenyl, octenyl, nonenyl, decenyl, undecenyl, and dodecenyl); a cycloalkyl group having 3 to 10 carbon atoms (for example, cyclopropyl, cyclobutyl, cyclopentyl, cyclohexyl, and cycloheptyl); an aromatic ring group having 6 to 30 carbon atoms (for example, phenyl, naphthyl, biphenyl, phenanthryl, and anthracenyl), a hetero ring group (preferably a residue of a hetero ring containing at least one hetero atom selected from a nitrogen atom, an oxygen atom, and a sulfur atom, and for example, pyridyl, pyrimidyl, triazinyl, thienyl, furyl, pyrrolyl, pyrazolyl, imidazolyl, triazolyl, thiazolyl, oxazolyl, thiadiallyl, oxadiazolyl, quinolyl, and isoquinolyl); or a group formed of a combination thereof. The substituent group may have one or more substituent groups when it is possible, and examples of the substituent group include an alkoxy group, an alkoxy carbonyl group, a halogen atom, an ether group, an alkyl carbonyl group, a cyano group, a thioether group, a sulfoxide group, a sulfonyl group, an amide group, and the like.

Hereinafter, specific examples of the monohydric alcohol which is able to be used in the present invention will be described, but the present invention is not limited thereto.

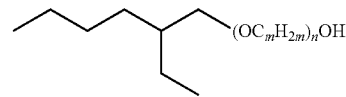

m = 2, n = 1: MA-1-2-1
m = 2, n = 2: MA-1-2-2
m = 3, n = 1: MA-1-3-1

$C_{18}H_{37}(OC_mH_{2m})_nOH$

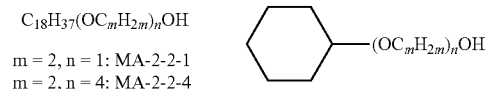

m = 2, n = 1: MA-2-2-1
m = 2, n = 4: MA-2-2-4
m = 3, n = 1: MA-2-3-1 m = 2, n = 1: MA-3-2-1

$C_2H_5(OC_mH_{2m})_nOH$    $CH_3(OC_mH_{2m})_nOH$ m = 2, n = 1: MA-4-2-1    m = 2, n = 1: MA-5-2-1
m = 2, n = 3: MA-4-2-3    m = 2, n = 2: MA-5-2-2
m = 4, n = 5: MA-4-4-5    m = 4, n = 8: MA-5-2-8

$C_4H_9(OC_mH_{2m})_nOH$

m = 2, n = 1: MA-7-2-1
m = 2, n = 2: MA-7-2-2
m = 2, n = 1: MA-6-2-1    m = 3, n = 3: MA-7-3-3

$C_{10}H_{21}(OC_mH_{2m})_nOH$

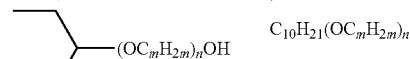

m = 2, n = 1: MA-9-2-1 m = 2, n = 1: MA-8-2-1

$C_{12}H_{26}(OC_mH_{2m})_nOH$    $C_{14}H_{29}(OC_mH_{2m})_nOH$ m = 2, n = 1: MA-10-2-1    m = 2, n = 1: MA-11-2-1

$C_{16}H_{33}(OC_mH_{2m})_nOH$    $C_{18}H_{37}(OC_mH_{2m})_nOH$ m = 2, n = 1: MA-12-2-1    m = 2, n = 1: MA-13-2-1

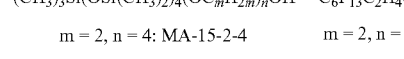

m = 2, n = 1: MA-14-2-1    m = 2, n = 1: MA-15-2-1
m = 2, n = 4: MA-15-2-4

$(CH_3)_3Si(OSi(CH_3)_2)_4(OC_mH_{2m})_nOH$    $C_6F_{13}C_2H_4(OC_mH_{2m})_nOH$ m = 2, n = 4: MA-15-2-4    m = 2, n = 4: MA-17-2-1

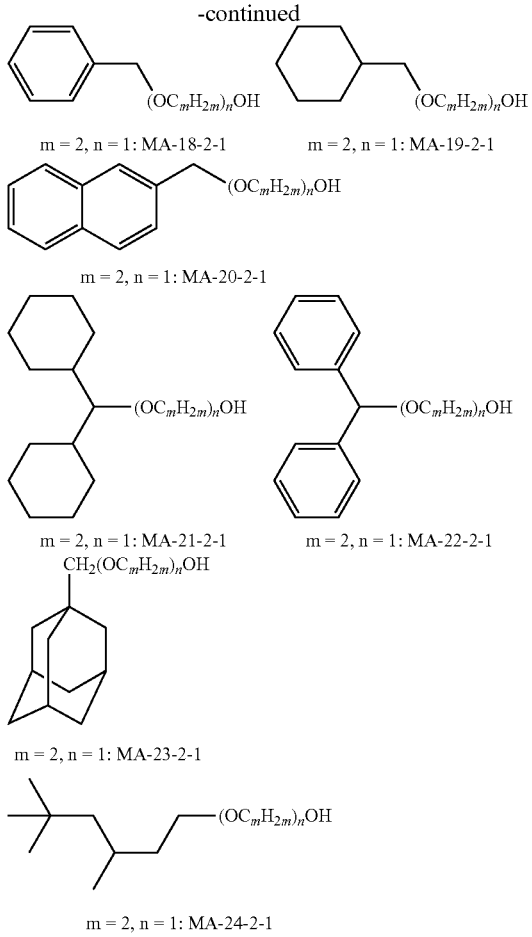

m = 2, n = 1: MA-18-2-1
m = 2, n = 1: MA-19-2-1
m = 2, n = 1: MA-20-2-1
m = 2, n = 1: MA-21-2-1
m = 2, n = 1: MA-22-2-1
m = 2, n = 1: MA-23-2-1
m = 2, n = 1: MA-24-2-1

(Organic Metal Compound)

The complex polyester composition of the present invention may contain at least one type of organic metal compound of an organic molybdenum compound and an organic zinc compound in addition to the polyester obtained by performing a reaction and condensation with respect to each of the compounds described above.

Examples of the organic molybdenum compound used in the present invention are able to include an organic molybdenum compound containing sulfur such as molybdenum dithiophosphate (also referred to as MoDTP) and molybdenum dithiocarbamate (also referred to as MoDTC); inorganic molybdenum compound (for example, molybdenum oxide such as molybdenum dioxide and molybdenum trioxide, a molybdic acid such as an orthomolybdic acid, a paramolybdic acid, (poly)molybdic sulfide, a metal salt of the molybdic acid, a molybdate such as an ammonium salt, molybdenum sulfide such as molybdenum disulfide, molybdenum trisulfide, molybdenum pentasulfide, and molybdenum polysulfide, molybdic sulfide, a metal salt or an amine salt of the molybdic sulfide, halogenated molybdenum such as molybdenum chloride, and the like); an organic compound containing sulfur (for example, alkyl (thio)xanthate, thiadiazole, mercaptothiadiazole, thiocarbonate, tetrahydrocarbylthiuram disulfide, bis(di(thio)hydrocarbyldithiophosphonate) disulfide, organic (poly)sulfide, ester sulfide, and the like) or a complex of other organic compounds and molybdenum, or a complex of the molybdenum compound containing sulfur such as molybdenum sulfide and molybdic sulfide and alkenyl succinic acid imide.

In addition, an organic molybdenum compound which does not contain sulfur as a constituent element is able to be used as the organic molybdenum compound. Specifically, examples of the organic molybdenum compound which does not contain sulfur as a constituent element include a molybdenum-amine complex, a molybdenum-succinic acid imide complex, a molybdenum salt of an organic acid, a molybdenum salt of alcohol, and the like, and among them, the molybdenum-amine complex, the molybdenum salt of the organic acid, and the molybdenum salt of the alcohol are preferable.

For example, methods disclosed in JP1986-87690A (JP-S61-87690A) and JP1986-106587A (JP-S61-106587A) are preferably used as a production method of MoDTP described above. That is, MoDTP is able to be obtained by allowing molybdenum trioxide or molybdate to react with alkali sulfide or alkali hydrosulfide, and then by adding $P_2S_5$ and secondary alcohol, and by performing a reaction at a suitable temperature. For example, a method disclosed in JP1981-12638B (JP-S56-12638B) is preferably used as the production method of MoDTC. That is, MoDTC is able to be obtained by allowing molybdenum trioxide or molybdate to react with alkali sulfide or alkali hydrosulfide, and then by adding carbon disulfide and secondary amine, and by performing a reaction at a suitable temperature.

Zinc dithiophosphate (ZDTP) which is the organic zinc compound used in the present invention is denoted by General Formula (3).

General Formula (3)

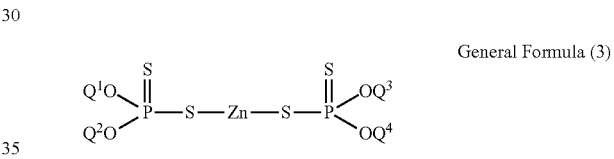

In General Formula (3), $Q^1$, $Q^2$, $Q^3$, and $Q^4$ may be identical to each other or different from each other, respectively, and it is preferable that $Q^1$, $Q^2$, $Q^3$, and $Q^4$ each independently represent an alkyl group having 4 to 20 carbon atoms such as an isopropyl group, a butyl group, an isobutyl group, a pentyl group, an isopentyl group, a neopentyl group, a hexyl group, a heptyl group, an octyl group, a 2-ethyl hexyl group, a nonyl group, a decyl group, an undecyl group, a dodecyl group, a tridecyl group, an isotridecyl group, a myristyl group, a palmityl group, and a stearyl group.

The organic metal compound may contain a metal salt or a metal-ligand complex. Here, it is preferable that the metal is molybdenum or zinc. Examples of the ligand are able to include a hydrocarbyl derivative of alcohol, polyol, glycerol, partial ester glycerol, thiol, carboxylate, carbamate, thiocarbamate, dithiocarbamate, phosphate, thiophosphate, dithiophosphate, amide, imide, amine, thiazole, thiadiazole, dithiazole, diazole, and triazole, and other polar molecule functional groups having an effective amount of 0, N, 5, or P respectively or by combining them. For example, it is preferable that the ligand is oxy molybdenum sulfide-N,N-di-octyl dithiocarbamate ($C_8$—Mo(DTC)), oxy molybdenum sulfide-N,N-di-tridecyl dithiocarbamate ($C_{16}$-Mo(DTC)), zinc n-butyl-n-pentyl dithiophosphate ($C_4/C_5$ ZnDTP), zinc di-2-ethyl hexyl dithiophosphate ($C_8$ ZnDTP), or zinc isopropyl-1-ethyl butyl dithiophosphate ($C_3/C_6$ ZnDTP). In addition, a Mo-containing compound such as Mo-dithiophosphate [Mo(DTP)], Mo-amine [Mo(Am)], Mo-alcoholate, and Mo-alcohol-amide is able to be exemplified as the ligand.

In the complex polyester composition of the present invention, when the organic molybdenum compound is used, the content of the organic molybdenum compound is preferably 10 ppm to 1000 ppm, is more preferably 50 ppm to 800 ppm, and is even more preferably 100 ppm to 600 ppm, with respect to the total mass of the composition. In addition, when the organic zinc compound is used, the content of the organic zinc compound is preferably 0.01 mass % to 5 mass %, is more preferably 0.05 mass % to 3 mass %, and is even more preferably 0.08 mass % to 1 mass %, with respect to the total mass of the composition. By setting the content of the organic metal compound to be in the range described above, it is possible to increase stability of the complex polyester composition, and it is possible to exhibit more excellent lubrication performance.

(Other Compounds)

In the present invention, other components may be used in the condensation reaction in addition to the polyhydric alcohol, the polycarboxylic acid, and the monohydric alcohol, and a complex polyester composition containing polyester to be obtained is also preferably used. In addition, other compounds may be mixed in addition to the organic metal compound described above.

(Polyester)

The complex polyester composition of the present invention contains the polyester which is obtained by mixing the polyhydric alcohol, the polycarboxylic acid, and the monohydric alcohol as described above, and by condensing the mixture. It is preferable that at least one type of polyester obtained by condensing the mixture is denoted by General Formula (a) described below.

General Formula (a)

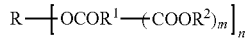

$$R \!-\!\!\left[OCOR^1\!-\!(COOR^2)_m\right]_n$$

Here, in General Formula (a), R represents a n-valent atomic group, $R^1$ represents a (m+1)-valent or more chain or cyclic aliphatic linking group or an aromatic linking group having carbon atoms of greater than or equal to 3, and $R^2$ represents a group having an oxyalkylene structure. In addition, n represents an integer of 2 to 4, and m represents an integer of 1 to 3.

In General Formula (a) described above, R represents a bivalent to hexavalent atomic group. In General Formula (a), it is preferable that n is an integer of 3 or 4, and it is preferable that R is a trivalent to tetravalent atomic group. That is, it is preferable that the polyhydric alcohol is a compound having three or more hydroxyl groups.

In General Formula (a), m represents an integer of 1 to 3, and is preferably represents an integer of 1 or 2. That is, it is preferable that the polycarboxylic acid is a bivalent or trivalent polycarboxylic acid.

In General Formula (a), the number of carbon atoms of R is preferably 2 to 20, is more preferably 2 to 15, is even more preferably 2 to 10, is still more preferably 2 to 7, and is particularly preferably 3 to 6.

It is preferable that an atom configuring an atomic group R is a carbon atom, a hydrogen atom, and an oxygen atom. It is preferable that R is an aliphatic hydrocarbon atomic group which may have a substituent group or an aromatic hydrocarbon atomic group which may have a substituent group. Among them, it is particularly preferable that R is an atomic group formed of saturated aliphatic hydrocarbon which may have a substituent group. According to the configuration of R described above, it is possible to obtain a complex polyester composition having excellent lubrication performance.

$R^1$ represents a residue of the polycarboxylic acid. Here, the residue of the polycarboxylic acid indicates a group configuring a portion excluding a carboxyl group from the polycarboxylic acid. In particular, it is preferable that $R^1$ is a dimer acid residue or a trimer acid residue.

The number of carbon atoms of $R^1$ is greater than or equal to 3, is preferably greater than or equal to 6, and is more preferably greater than or equal to 8. In addition, the number of carbon atoms of $R^1$ is preferably less than or equal to 64, is more preferably less than or equal to 58, and is even more preferably less than or equal to 46. Among them, it is preferable that the number of carbon atoms of $R^1$ is 20 to 46.

$R^2$ represents a group having an oxyalkylene structure. That is, it is preferable that $R^2$ is a branch alkyl group or an alkyl group having an ether bond in a chain. In addition, the number of carbon atoms of $R^2$ is preferably greater than or equal to 6, is more preferably greater than or equal to 8, and is even more preferably greater than or equal to 10.

When the compound of the polyhydric alcohol, the polycarboxylic acid, and the monohydric alcohol are mixed, it is preferable that the equivalence ratio of mixing the polycarboxylic acid with respect to the polyhydric alcohol is 1 to 4, and an equivalence ratio of mixing the monohydric alcohol with respect to the polyhydric alcohol is 0.5 to 5. That is, it is preferable that the mixing ratio is Polyhydric Alcohol:Polycarboxylic Acid:Monohydric Alcohol=1:1 to 4:0.5 to 5. The mixing ratio is more preferably 1:2.0 to 4:1.5 to 5, and is even more preferably 1:2.2 to 4:2.5 to 5. In particular, it is preferable that a side chain of the polyester is end capped, and thus it is preferable that the total equivalent weights of the polyhydric alcohol and the monohydric alcohol are greater than or equal to the equivalent weight of the polycarboxylic acid.

It is preferable that the viscosity of the complex polyester composition of the present invention at 40° C. is 50 mPa·s to 1650 mPa·s. The viscosity of the complex polyester composition at 40° C. is preferably greater than or equal to 50 mPa·s, is more preferably greater than or equal to 70 mPa·s, is even more preferably greater than or equal to 100 mPa·s. In addition, the viscosity of the complex polyester composition at 40° C. is preferably less than or equal to 1650 mPa·s, is more preferably less than or equal to 1200 mPa·s, and is even more preferably less than or equal to 1000 mPa·s. By setting the viscosity of the complex polyester composition to be in the range described above, it is possible to suppress a friction coefficient of the complex polyester composition to be low, and thus it is possible to increase the lubrication performance.

The complex polyester composition of the present invention has the configuration as described above, and thus has excellent characteristics such as a small increase in the friction coefficient from general fluid lubrication or an elastic fluid lubrication region to an extreme pressure region. It is considered that such an excellent effect is obtained by having a stereoscopic structure of the polyester obtained in the present invention in which side chains are radially arranged. The polyester obtained in the present invention is a compound configured of the polyhydric alcohol which is able to radially arrange the side chains, the polycarboxylic acid which is connected to the polyhydric alcohol and is radially stretched, and the monohydric alcohol which is a terminal linking group of the polycarboxylic acid. In the present invention, the polyester has the side chain by using the polyhydric alcohol as a center atomic group, and thus it is possible to ensure a large free volume by the stereoscopic structure. Accordingly, it is possible to suppress an increase in the viscosity and the friction coefficient of the compound even when under high pressure.

In the present invention, the component having a weight average molecular weight of less than or equal to 2000 in the GPC chart contains an ester component denoted by General Formula (2) described below.

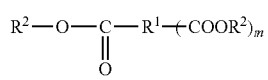

General Formula (2)

Here, in General Formula (2), $R^1$ represents a (m+1)-valent or more chain or cyclic aliphatic linking group or an aromatic linking group, and $R^2$ represents a group having an oxyalkylene structure. In addition, m represents an integer of 1 to 3. Furthermore, specific groups which are able to be included in $R^1$ and $R^2$ are identical to the groups exemplified in $R^1$ and $R^2$ of General Formula (a).

In the component having a weight average molecular weight of less than or equal to 2000 in the GPC chart, a light component may be further contained in addition to the ester component denoted by General Formula (2) described above. However, in the present invention, the component having a weight average molecular weight of less than or equal to 2000 in the GPC chart is contained such that the component is less than or equal to 43 area %. Accordingly, it is possible to exhibit high lubrication performance under general conditions, as well as under extreme pressure conditions.

In the present invention, unreacted COOH in the polycarboxylic acid may remain in the side chain of the polyester contained in the complex polyester composition, and unreacted OH in the polyhydric alcohol or the monohydric alcohol may remain in the side chain, and when OH and COOH remain in the side chain, a hydroxyl value and an acid value increases, and thus OH and COOH remaining in the side chain may not be preferable according to the application (for example, the application of a lubricant, and the like). In such a case, OH and COOH in the polyester are eliminated by a separate acylation treatment and/or an esterification treatment, and thus the hydroxyl value and the acid value are able to be reduced.

In order to eliminate OH in the polyester, polyester in which OH remains in a side chain is obtained, and then a treatment is able to be performed in which at least a part of the polyester is acylated. The acylation treatment is a treatment in which a monobasic acid ($R^1$COOH) or a monobasic acid anhydride (($R^1$CO)$_2$O) is added to the polyester having OH remaining therein and is heated, and thus remaining OH is converted into OCOR$^1$. It is preferable that the hydroxyl value is reduced by the acylation treatment from a viewpoint of easy mixing properties of the polyester at the time of being mixed with other oily mediums.

In addition, a treatment of eliminating COOH in polyester may be performed. For example, esterification is able to be performed by treating the polyester with diazomethane or the like.

A ratio of unreacted OH in the polyester is determined by measuring $^{13}$C-NMR. In the application of a lubricant, a residual ratio of OH in the polyester is preferably 0% to 40%, is more preferably 0% to 35%, and is even more preferably 0% to 30%. In addition, in the application of a lubricant, the acid value of the polyester (the number of mg of KOH required for neutralizing 1 g of a sample) is preferably 0 to 50, is more preferably 0 to 40, and is even more preferably 0 to 30. However, the present invention is not limited to the range described above.

(Production Method for Complex Polyester Composition)

The complex polyester composition of the present invention is able to be obtained by performing dehydration condensation at least three raw materials of the polyhydric alcohol, the polycarboxylic acid, and the monohydric alcohol described above in the absence of a solvent. Furthermore, in a producing step, two raw materials (for example, polyhydric alcohol and a polycarboxylic acid, or a polycarboxylic acid and monohydric alcohol) may react with each other in advance, and then the remaining raw material may react with the reacted raw materials.

Here, conditions of "in the absence of a solvent" indicate that a content ratio of the solvent is less than or equal to 1 mass % with respect to the total amount of the polyhydric alcohol, the polycarboxylic acid, and the monohydric alcohol, and containing a small amount of solvent of less than or equal to 1 mass % is included in the conditions of "in the absence of a solvent" in the present invention.

In addition, in the present invention, at least one type of organic metal compound of an organic molybdenum compound and an organic zinc compound may be mixed to the ester component obtained as described above.

A feed ratio (a mixing ratio) of the polyhydric alcohol, the polycarboxylic acid, and the monohydric alcohol is determined by an equivalent weight. Here, the equivalent weight indicates a chemical equivalent weight of COOH or OH in a reaction. When the number of OH groups in one molecule of the polyhydric alcohol is n, and the number of moles is M1, the equivalent weight of the polyhydric alcohol is defined by n×M1. Similarly, the number of COOH groups in one molecule of the polycarboxylic acid is m, and the number of moles is M2, the equivalent weight of the polycarboxylic acid is defined by m×M2. The number of OH groups in one molecule of the monohydric alcohol is 1, and thus when the number of moles is M3, the equivalent weight of the monohydric alcohol is defined by M3. The ratio described above is a ratio of n×M1, m×M2, and M3.

In the present invention, it is preferable that the mixing ratio is Polyhydric Alcohol:Polycarboxylic Acid:Monohydric Alcohol=1:1 to 4:0.5 to 5. The mixing ratio is more preferably 1:2.0 to 4:1.5 to 5, and is even more preferably 1:2.2 to 4:2.5 to 5. In particular, it is preferable that the side chain of the polyester is end capped, and thus it is preferable that the total equivalent weights of the polyhydric alcohol and the monohydric alcohol are greater than or equal to the equivalent weight of the polycarboxylic acid.

The mixture fed as described above is subjected to a dehydration condensation reaction in the presence of a catalyst or in the absence of a catalyst and in the absence of a solvent, and thus it is possible to obtain the complex polyester composition of the present invention.

The reaction is accelerated by using the catalyst, but a post treatment of removing the catalyst is complex, and causes coloration of a product, and thus it is preferable that the catalyst is not used. However, when the catalyst is used, general conditions and operations are used in general catalysts. In reference to this, it is possible to refer to the references disclosed in JP2001-501989A, JP2001-500549A, JP2001-507334A, and JP2002-509563A.

The reaction is performed after the feeding at a liquid temperature of 120° C. to 250° C., preferably 130° C. to 230° C., more preferably 130° C. to 220° C., and particularly preferably 140° C. to 220° C. It is preferable that the water generated by the reaction is removed.

In a reaction time, a theoretical amount of generated water is calculated from the number of moles of the fed materials, and thus it is preferable that the reaction is performed until the theoretical amount of generated water is obtained, but it is difficult to completely perform the reaction in this manner. Even when the reaction is performed until the theoretical amount of generated water is 60% to 90%, the complex polyester composition has excellent lubrication properties. The reaction time is 1 hour to 24 hours, is preferably 3 hours to 18 hours, is more preferably 5 hours to 18 hours, and is most preferably 6 hours to 15 hours.

After the dehydration condensation is performed and a volatile component is removed, remaining OH may be further acylated. When the acylation is performed, a suitable amount of monobasic acid ($R^1COOH$) or monobasic acid anhydride (($R^1CO)_2O$), and preferably monobasic acid anhydride (($R^1CO)_2O$) is added and is heated to a temperature of preferably higher than or equal to 100° C., more preferably higher than or equal to 120° C., and particularly preferably higher than or equal to 150° C., and thus at least a part of remaining OH, and preferably almost all of remaining OH is able to be converted to $OCOR^1$. It is preferable that the volatile component which is by-produced is removed by distillation described below. Furthermore, $R^1$ is an alkyl group or an aryl group having 1 to 10 carbon atoms, is more preferably an alkyl group or an aryl group having 1 to 6 carbon atoms, and is even more preferably a methyl group, an ethyl group, a butyl group, and a phenyl group, and among them, the methyl group or the phenyl group is preferable, and the methyl group is particularly preferable.

In addition, in order to eliminate remaining COOH, an esterification treatment may be performed after the dehydration condensation is performed and the volatile component is removed. The esterification treatment, for example, is able to be performed by adding diazomethane, and at least a part of COOH, and preferably almost all of COOH, is able to be converted into methyl ester.

According to this reaction, it is possible to obtain a complex polyester composition which contains the predetermined polyester, and a light component containing at least ester generated as described above. After the dehydration condensation reaction is performed, as necessary, the acylation treatment and/or the esterification treatment are performed, and then the obtained complex polyester composition is able to be directly used in various applications, for example, as a lubricant. In addition, according to the application, various treatments may be performed.

It is preferable that filtration is performed after the reaction and the treatment after the reactions are performed, and thus waste and the like are removed. Furthermore, when complex polyester is a solid, it is possible to obtain the complex polyester composition by melting the solid complex polyester or by reprecipitating the solid complex polyester as a powder.

(Lubricant Composition)

The present invention may relate to a lubricant composition containing at least the complex polyester composition obtained by the method described above. For example, the complex polyester composition of the present invention, along with various additives and/or mediums is able to be added to the lubricant composition.

Examples of the additive are able to include one type or two or more types of additives selected from an abrasion preventing agent, a viscosity index improver, an antioxidant, a cleaning agent, a dispersant, a fluidizing agent, a curing agent, a corrosion preventing agent, a seal compatible agent, a defoaming agent, a rust preventing agent, a friction adjuster, and a thickener.

By adding such an additive, a preferred function as a lubricant, such as suppression in abrasion, is able to be imparted to the lubricant composition. Lubricants which are able to be used in the present invention are able to refer to the description in paragraphs "0098" to "0165" of JP2011-89106A.

In addition, examples of the medium are able to include one type or two or more types of mediums selected from mineral oil, a fatty oil compound, polyolefin oil, silicone oil, ether oil (preferably perfluoropolyether oil and diphenyl ether oil), and ester oil (preferably aromatic ester oil, aliphatic monoester oil, aliphatic diester oil, and polyol ester lubricating oil).

In the present invention, the "medium" indicates all mediums generally referred to as a "flowable liquid". However, it is not necessary that the medium is in a liquid state at room temperature or at a temperature to be used, and a material in any state of a solid, a gel, and the like in addition to the liquid is able to be used. The medium used in the present invention is not particularly limited, but is able to be selected from various liquids according to the application. The mediums which are able to be used in the present invention are able to refer to the description in paragraphs "0067" to "0096" of JP2011-89106A.

Hydrocarbon-based base oil in which a lubricating oil fraction obtained by performing atmospheric pressure distillation and/or reduced pressure distillation with respect to crude oil is refined by only one type or a combination of two or more types of refine treatments such as solvent deasphalting, solvent extraction, hydrogenation decomposition, solvent dewaxing, contact dewaxing, hydrogenation refinement, washing with sulfuric acid, and a white clay treatment is preferably used as the medium.

Base oil in which a ratio (CA/CB) of a ratio (CA) of a component having carbon atoms of less than or equal to 24 in a carbon number distribution obtained by gas chromatic distillation to a ratio (CB) of a component having carbon atoms of greater than or equal to 25 in a carbon number distribution obtained by gas chromatic distillation is greater than or equal to 2.0 is preferably used as the hydrocarbon-based base oil. CA/CB is preferably greater than or equal to 2.5, is more preferably greater than or equal to 3, and most preferably greater than or equal to 5. By setting CA/CB to be in the range described above, it is possible to obtain sufficient low high-temperature and high-shear (HTHS) viscosity at 80° C.

In addition, it is preferable that the hydrocarbon-based base oil is hydrocarbon-based base oil in which a ratio CC/CD of a ratio (CC) of a component having a carbon atoms of less than or equal to 18 in a carbon number distribution obtained by gas chromatic distillation to a ratio (CD) of a component having carbon atoms of greater than or equal to 19 in a carbon number distribution obtained by gas chromatic distillation is less than or equal to 0.3. CC/CD is preferably less than or equal to 0.25, is more preferably less than or equal to 0.2, and is most preferably less than or equal to 0.1. By setting CC/CD to be in the range described above, it is possible to suppress the consumption of lubricating oil even in an engine for a power generator.

Here, the gas chromatic distillation was performed in the following conditions.
Model: GC-2010 manufactured by Shimadzu Corporation
Column: Ultra Alloy-1 HT (30 mm×0.25 mmΦ)

Carrier Gas: Helium 200 kPa
Detector: FID
Det. Temp.: 350° C.
Oven Temp.: 80° C. to 320° C. (5 min)
Temp. Rate: 5° C./min
Inj. Vol: 1 μL of Toluene Solution Mineral oil-based base oil which is obtained by using the following base oils (1) to (8) as a raw material, by refining the raw material oil and/or a lubricating oil fraction collected from the raw material oil by a predetermined refinement method, and by collecting the lubricating oil fraction is able to be used as a medium.

(1) Distillate oil obtained by performing atmospheric pressure distillation with respect to paraffin-based crude oil and/or mix group-based crude oil (2) Distillate oil (WVGO) obtained by performing reduced pressure distillation with respect to residual oil of atmospheric pressure distillation of paraffin-based crude oil and/or mix group-based crude oil (3) Synthetic wax (Fischer Tropsch wax, GTL wax, and the like) obtained by wax obtained from a lubricating oil dewaxing step (slack wax or the like) and/or gas to liquid (GTL) process or the like (4) Mild hydrocracking treated oil of one type or two or more types of mixed oils and/or mixed oil selected from the base oils (1) to (3)

(5) Two or more types of mixed oils selected from the base oils (1) to (4)

(6) Deasphalted oil (DAO) of the base oil (1), (2), (3), (4), or (5)

(7) Mild hydrocracking treated oil (MHC) of the base oil (6)

(8) Two or more types of mixed oils selected from the base oils (1) to (7).

Furthermore, hydrogenation refinement such as hydrogenation decomposition and hydrofinishing; solvent refinement such as furfural solvent extraction; dewaxing such as solvent dewaxing or contact dewaxing; white clay refinement of acidic white clay or active white clay; washing with chemicals (acid or alkali) such as washing with a sulfuric acid and washing with caustic soda, and the like are preferable as the predetermined refinement method. In the present invention, one type of refinement method may be independently performed, or two or more types thereof may be performed by being combined. In addition, when two or more types of refinement methods are combined, the sequence is not particularly limited, but is able to be suitably selected.

Further, the following base oil (9) or (10) which is obtained by performing a predetermined treatment with respect to base oil selected from the base oils (1) to (8) or a lubricating oil fraction collected from the base oil is particularly preferable as a medium.

(9) Hydrogenation decomposition mineral oil obtained by performing hydrogenation decomposition with respect to base oil selected from the base oils (1) to (8) or a lubricating oil fraction collected from the base oil, and by performing a dewaxing treatment such as solvent dewaxing or contact dewaxing or performing dewaxing treatment and then distillation with respect to a product of the hydrogenation decomposition or a lubricating oil fraction collected from the product.

(10) Hydroisomerization mineral oil obtained by performing hydroisomerization with respect to base oil selected from the base oils (1) to (8) or a lubricating oil fraction collected from the base oil, and by performing a dewaxing treatment such as solvent dewaxing or contact dewaxing or performing dewaxing treatment and then distillation with respect to a product of the hydroisomerization or a lubricating oil fraction collected from the product by distillation or the like.

In addition, when the medium of (9) or (10) described above is obtained, as necessary, a solvent refine treatment and/or hydrofinishing treatment step may be further provided in a suitable step.

The kinematic viscosity of the mineral oil-based base oil at 100° C. is preferably less than or equal to 10 mm$^2$/s, is more preferably less than or equal to 9 mm$^2$/s, is even more preferably less than or equal to 8 mm$^2$/s, and is most preferably less than or equal to 7 mm$^2$/s. On the other hand, the kinematic viscosity at 100° C. is preferably greater than or equal to 1 mm$^2$/s, is more preferably greater than or equal to 1.5 mm$^2$/s, is even more preferably greater than or equal to 2 mm$^2$/s, and is most preferably greater than or equal to 2.3 mm$^2$/s.

Here, the kinematic viscosity at 100° C. indicates kinematic viscosity at 100° C. defined in ASTM D-445.

It is preferable that mineral oil-based base oil in which the kinematic viscosity at 100° C. is in the following range is collected by distillation or the like, and is used as a medium. Furthermore, (I) and (II) are able to be used by being mixed, but it is preferable that (I) is independently used.

(I) Mineral oil-based base oil in which the kinematic viscosity at 100° C. is greater than or equal to 1 mm$^2$/s, and is preferably greater than or equal to 2.3 mm$^2$/s, and is less than 3 mm$^2$/s, and is preferably less than or equal to 2.9 mm$^2$/s (II) Mineral oil-based base oil in which the kinematic viscosity at 100° C. is greater than or equal to 3 mm$^2$/s, and is preferably greater than or equal to 3.5 mm$^2$/s, and is less than or equal to 4.5 mm$^2$/s, and is preferably less than or equal to 4.0 mm$^2$/s The viscosity index of the mineral oil-based base oil is preferably greater than or equal to 90, is more preferably greater than or equal to 105, and is even more preferably greater than or equal to 110. In addition, it is preferable that the viscosity index of the mineral oil-based base oil is less than or equal to 160. In addition, the viscosity index of the mineral oil-based base oil (I) is preferably greater than or equal to 90, is more preferably greater than or equal to 105, is even more preferably greater than or equal to 110, and is most preferably greater than or equal to 120. In addition, it is preferable that the viscosity index of the mineral oil-based base oil (I) is less than or equal to 160. In addition, the viscosity index of the mineral oil-based base oil (II) is preferably greater than or equal to 110, is more preferably greater than or equal to 120, is even more preferably greater than or equal to 130, and is most preferably greater than or equal to 140. In addition, it is preferable that the viscosity index of the mineral oil-based base oil (II) is less than or equal to 160. By setting the viscosity index of the mineral oil-based base oil to be in the range described above, viscosity-temperature properties, heat and oxidation stability, and volatilization preventing properties are enhanced, and abrasion preventing properties are improved.

Furthermore, the viscosity index in the present invention indicates a viscosity index measured on the basis of JIS K 2283-1993.

In addition, density ($\rho_{15}$) of the mineral oil-based base oil at 15° C. depends on viscosity grade of a base oil component of the lubricating oil, and it is preferable that the density ($\rho_{15}$) of the mineral oil-based base oil at 15° C. is set to be less than or equal to the value of ρ denoted by the following expression, that is, $\rho_{15} \leq \rho$.

$$\rho = 0.0025 \times kv100 + 0.816$$

In the expression, kv100 indicates the kinematic viscosity (mm$^2$/s) of the base oil component of the lubricating oil at 100° C.

Furthermore, by setting the density ($\rho_{15}$) of the mineral oil-based base oil at 15° C. to be in the range described above, viscosity-temperature properties, heat and oxidation stability, volatilization preventing properties are enhanced, and low temperature viscosity properties are able to be improved.

Specifically, the density ($\rho_{15}$) of the mineral oil-based base oil at 15° C. is preferably less than or equal to 0.880, is more preferably less than or equal to 0.870, is even more preferably less than or equal to 0.860, and is most preferably less than or equal to 0.850, and is preferably greater than or equal to 0.785. Furthermore, the density at 15° C. in the present invention indicates density measured at 15° C. on the basis of JIS K 2249-1995.

(Properties of Lubricant Composition)

The viscosity of the lubricant composition of the present invention at 40° C. is preferably less than or equal to 1650 mPa·s, is more preferably less than or equal to 1200 mPa·s, and is even more preferably less than or equal to 1000 mPa·s. Suitable viscosity is obtained according to a use environment, and thus it is necessary that the viscosity is matched to the use environment.

The constituent elements of the lubricant composition of the present invention are preferably configured only of carbon, hydrogen, oxygen, and nitrogen, and are more preferably configured only of carbon, hydrogen, and oxygen. In addition, oil used as an oily medium has various materials configured only of carbon, hydrogen, and oxygen. By combining these materials, it is possible to prepare a composition in which the constituent elements are configured only of carbon, hydrogen, oxygen, and nitrogen.

Furthermore, current lubricating oil generally contains phosphorus, sulfur, and heavy metal. Lubricating oil used in a two-stroke engine in which the lubricating oil is combusted along with the fuel does not contain phosphorus and heavy metal in consideration of an environmental load, but sulfur is present in lubricating oil used in a four-stroke engine in the amount of approximately half of the lubricating oil. That is, in a current lubrication technology, it is assumed that it is essential to form a boundary lubrication film by using the least amount of sulfur, but a load on a catalyst for purifying exhaust gas is extremely considerable by containing a sulfur element. In the catalyst for purifying the exhaust gas, platinum or nickel is used, but a poisoning function of phosphorus or sulfur becomes a significant problem. From this viewpoint, it is extremely advantageous that the elements configuring the composition of the lubricating oil are configured only of carbon, hydrogen, oxygen, and nitrogen. Further, the lubricating oil configured only of carbon, hydrogen and oxygen is optimized for lubricating oil of an industrial machine, in particular, an associated apparatus for processing food other than the engine oil. In the current technology, an element composition is used in which friction coefficient is sacrificed in consideration of the environment. This is a technology which is extremely preferable even in lubricating oil for machining and working metal which require a large amount of water for cooling.

(Preparation Method of Lubricant Composition)

The lubricant composition of the present invention is able to be prepared by adding the complex polyester composition into an oily medium or an aqueous medium, and by dissolving and/or dispersing the complex polyester composition therein. The dissolving and/or dispersing may be performed in under heating. It is preferable that the added amount of the complex polyester composition is greater than or equal to 10 mass % with respect to the mass of the oily medium. However, the present invention is not limited to the range described above, and the compound described above may not be in the range described above insofar as the amount of the complex polyester composition is sufficient for exhibiting a friction reducing function.

(Application of Lubricant Composition)

The lubricant composition of the present invention is useful as a lubricant. That is, the present invention relates to a lubricant containing the complex polyester composition described above or a lubricant containing the lubricant composition described above.

The lubricant of the present invention, for example, is supplied between two sliding surfaces, and thus is able to be used for reducing friction. The composition of the present invention is able to form a film on the sliding surface. The material of the sliding surface is iron steel, and specifically, examples of the material of the sliding surface include carbon steel for a structure machine use, alloy steel for a structure machine use such as a nickel chromium steel material, a nickel chromium molybdenum steel material, a chromium steel material, a chromium molybdenum steel material, and an aluminum chromium molybdenum steel material, stainless steel, maraging steel, and the like.

Various metals other than iron steel, or an inorganic material or an organic material other than metal are widely used as the material of the sliding surface. Examples of the inorganic material or the organic material other than metal include various plastics, ceramics, carbons, and mixtures thereof. More specifically, examples of a metal material other than iron steel include cast iron, a copper•copper-lead•aluminum alloy, and cast metal and white metal thereof.

Furthermore, the materials of the sliding surface are able to refer to the description in paragraphs "0168" to "0175" of JP2011-89106A.

The lubricant of the present invention is able to be used in various applications. For example, the lubricant of the present invention is able to be used as lubricating oil for grease, a releasing agent, engine oil for an internal combustion engine, oil for metal working (machining), oil for a bearing, fuel for a combustion engine, vehicle engine oil, gear oil, operating oil for an automobile, lubricating oil for a vessel and an aircraft, machine oil, turbine oil, hydraulic operating oil, compressor and vacuum pump oil, freezer oil, lubricating oil for metal working, a lubricant for magnetic recording medium, a lubricant for a micro machine, a lubricant for an artificial bone, shock absorber oil, or rolling oil. Further, the lubricant of the present invention is also used in an air conditioner or a refrigerator including a reciprocating type or rotating type airtight compressor, an air conditioner or a dehumidifier for an automobile, a cooling device such as a freezer, a freezing refrigerating warehouse, a vending machine, a showcase, a chemical plant, and the like.

The lubricant of the present invention is useful as lubricating oil for metal working which does not contain a chlorine-based compound, for example, when a metal material such as an iron and steel material or an Al alloy is subjected to hot rolling, or is subjected to working such as machining, and is useful as metal working oil or metal plastic working oil such as cold rolling oil, machining oil, grinding oil, drawing oil, and press working oil of aluminum, and in particular, is useful as an inhibitor against abrasion, damage, and surface roughness at the time of performing high-speed and high-load working, and is useful as a metal working oil composition which is able to be applied to low-speed heavy machining such as broach working and gun drill working.

In addition, the lubricant of the present invention is able to be used in various lubricating oils for grease, a lubricant for magnetic recording medium, a lubricant for a micro machine, a lubricant for an artificial bone, and the like. In addition, it is possible to configure the element composition of the lubricant composition as a carbohydrate, and thus, for example, a composition in which sorbitan fatty acid ester containing polyoxy ethylene ether which is widely used in cake mix, salad dressing, shortening oil, chocolate, and the like as an emulsifier, a dispersant, and a solubilizer is used as base oil of edible oil is configured as lubricating oil, and therefore, high-performance lubricating oil which is entirely harmless to a human body is able to be used in the lubrication of a manufacturing device in a food manufacturing line or a medical instrument member.

Further, the composition of the present invention is dispersed by being emulsified in water system or is dispersed in a polar solvent or a resin medium, and thus is able to be used as machining oil or rolling oil.

In addition, the lubricant composition of the present invention is able to be used as a releasing agent in various applications. For example, the lubricant composition of the present invention is used as a releasing agent of a polycarbonate resin, a flame retardant polycarbonate resin, a crystalline polyester resin which is a main component of a toner for forming an image used in an electrophotographic device, an electrostatic recording device, and the like, a thermoplastic resin composition for various moldings, an epoxy resin composition for sealing a semiconductor, and the like. In one aspect of the releasing agent, the content of the complex polyester composition is 0.01 parts by mass to 10 parts by mass (preferably 0.1 parts by mass to 5 parts by mass) with respect to 100 parts by mass of a resin such as a polycarbonate resin.

In addition, the lubricant of the present invention is kneaded into or is applied onto a fiber product of a clothing material or the like in advance, and thus is able to be used as a stain-proofing agent which accelerates removal of stain attached onto the fiber product and prevents the fiber product from being stained.

EXAMPLE

Hereinafter, the present invention will be more specifically described with reference to examples. Materials, used amounts, ratios, treatment contents, treatment sequences, and the like of the following examples are able to be suitably changed unless the changes cause deviance from the gist of the present invention. Accordingly, the range of the present invention will not be limited to the following specific examples.

Examples 1 to 8

Synthesis of Polyester

Polyhydric alcohol, a polycarboxylic acid, and monohydric alcohol shown in Table 1 were put into a reaction vessel which was attached with a Dean-Stark dehydration device such that the amount of each material was as shown in Table 1. After that, the mixture was stirred at a liquid temperature of 160° C. to 220° C. and a nitrogen flow rate of 0.5 L/min for 10 hours. Water, which was generated during the stirring, was removed. The mixture was allowed to stand to cool to room temperature, and thus a complex polyester composition was obtained as a yellow transparent liquid material.

Comparative Examples 1 to 8

Polyesters of Comparative Examples 1 to 8 were synthesized by the same conditions as described above except that toluene was used as a solvent in the same parts by weight as that of the polyhydric alcohol, and the reaction was performed at the liquid temperature of 200° C.

TABLE 1

|  | Polyhydric Alcohol Number | | Polycarboxylic Acid Number | | Monohydric Alcohol Number | |
| --- | --- | --- | --- | --- | --- | --- |
| Compound Number | Type | Mixing Amount (Equivalence Ratio) | Type | Mixing Amount (Equivalence Ratio) | Type | Mixing Amount (Equivalence Ratio) |
| Compound-1 | PA-2 | 1 | CA-8 | 2.2 | MA-1-2-1 | 2.5 |
| Compound-2 | PA-2 | 1 | CA-8 | 3 | MA-8-2-1 | 2.7 |
| Compound-3 | PA-2 | 1 | CA-8 | 2.4 | MA-15-2-4 | 3 |
| Compound-4 | PA-2 | 1 | CA-9 | 2.4 | MA-1-2-1 | 3.5 |
| Compound-5 | PA-2 | 1 | CA-9 | 3 | MA-6-2-1 | 4 |
| Compound-6 | PA-2 | 1 | CA-9 | 3.5 | MA-19-2-1 | 4 |
| Compound-7 | PA-13 | 1 | CA-4 | 2.2 | MA-1-2-1 | 3 |
| Compound-8 | PA-13 | 1 | CA-6 | 3.2 | MA-1-2-4 | 3 |
| Compound-9 | PA-13 | 1 | CA-7 | 4 | MA-15-2-4 | 4 |
| Compound-10 | PA-13 | 1 | CA-8 | 2.5 | MA-1-2-1 | 3 |
| Compound-11 | PA-13 | 1 | CA-8 | 2.2 | MA-1-2-2 | 3 |
| Compound-12 | PA-13 | 1 | CA-8 | 2.6 | MA-5-2-1 | 3 |
| Compound-13 | PA-13 | 1 | CA-8 | 3 | MA-5-2-2 | 4 |
| Compound-14 | PA-13 | 1 | CA-8 | 3 | MA-6-2-1 | 3 |
| Compound-15 | PA-13 | 1 | CA-8 | 2.6 | MA-15-2-4 | 3 |
| Compound-16 | PA-13 | 1 | CA-8 | 2.3 | MA-19-2-1 | 4 |
| Compound-17 | PA-13 | 1 | CA-9 | 3.5 | MA-1-2-1 | 4 |
| Compound-18 | PA-13 | 1 | CA-9 | 4 | MA-1-2-2 | 4 |
| Compound-19 | PA-13 | 1 | CA-9 | 3.1 | MA-5-2-1 | 3 |
| Compound-20 | PA-13 | 1 | CA-9 | 2.4 | MA-5-2-2 | 3 |
| Compound-21 | PA-13 | 1 | CA-9 | 2.4 | MA-6-2-1 | 3 |
| Compound-22 | PA-13 | 1 | CA-9 | 2.6 | MA-15-2-4 | 3 |

TABLE 1-continued

| Compound Number | Polyhydric Alcohol Number | | Polycarboxylic Acid Number | | Monohydric Alcohol Number | |
|---|---|---|---|---|---|---|
| | Type | Mixing Amount (Equivalence Ratio) | Type | Mixing Amount (Equivalence Ratio) | Type | Mixing Amount (Equivalence Ratio) |
| Compound-23 | PA-13 | 1 | CA-11 | 2.5 | MA-1-2-2 | 4 |
| Compound-24 | PA-13 | 1 | CA-18 | 2.8 | MA-1-3-1 | 4 |
| Compound-25 | PA-13 | 1 | CA-20 | 2.5 | MA-6-2-1 | 3 |
| Compound-26 | PA-13 | 1 | CA-21 | 3 | MA-19-2-1 | 4 |
| Compound-27 | PA-14 | 1 | CA-4 | 2.2 | MA-1-2-1 | 3 |
| Compound-28 | PA-14 | 1 | CA-6 | 3.2 | MA-1-2-4 | 3 |
| Compound-29 | PA-14 | 1 | CA-7 | 4 | MA-15-2-4 | 4 |
| Compound-30 | PA-14 | 1 | CA-8 | 2.5 | MA-1-2-1 | 3 |
| Compound-31 | PA-14 | 1 | CA-8 | 2.2 | MA-1-2-2 | 3 |
| Compound-32 | PA-14 | 1 | CA-8 | 2.6 | MA-5-2-1 | 3 |
| Compound-33 | PA-14 | 1 | CA-8 | 3 | MA-5-2-2 | 4 |
| Compound-34 | PA-14 | 1 | CA-8 | 3 | MA-6-2-1 | 3 |
| Compound-35 | PA-14 | 1 | CA-8 | 2.6 | MA-15-2-4 | 3 |
| Compound-36 | PA-14 | 1 | CA-8 | 2.3 | MA-19-2-1 | 4 |
| Compound-37 | PA-14 | 1 | CA-9 | 3.5 | MA-1-2-1 | 4 |
| Compound-38 | PA-14 | 1 | CA-9 | 4 | MA-1-2-2 | 4 |
| Compound-39 | PA-14 | 1 | CA-9 | 3.1 | MA-5-2-1 | 3 |
| Compound-40 | PA-14 | 1 | CA-9 | 2.4 | MA-5-2-2 | 3 |
| Compound-41 | PA-14 | 1 | CA-9 | 2.4 | MA-6-2-1 | 3 |
| Compound-42 | PA-14 | 1 | CA-9 | 2.6 | MA-15-2-4 | 3 |
| Compound-43 | PA-14 | 1 | CA-11 | 2.5 | MA-1-2-2 | 4 |
| Compound-44 | PA-14 | 1 | CA-18 | 2.8 | MA-1-3-1 | 4 |
| Compound-45 | PA-14 | 1 | CA-20 | 2.5 | MA-6-2-1 | 3 |
| Compound-46 | PA-14 | 1 | CA-21 | 3 | MA-19-2-1 | 4 |
| Compound-47 | PA-15 | 1 | CA-4 | 2.2 | MA-1-2-1 | 3 |
| Compound-48 | PA-15 | 1 | CA-6 | 3.2 | MA-1-2-4 | 3 |
| Compound-49 | PA-15 | 1 | CA-7 | 4 | MA-15-2-4 | 4 |
| Compound-50 | PA-15 | 1 | CA-8 | 2.5 | MA-1-2-1 | 3 |
| Compound-51 | PA-15 | 1 | CA-8 | 2.2 | MA-1-2-2 | 3 |
| Compound-52 | PA-15 | 1 | CA-8 | 2.6 | MA-5-2-1 | 3 |
| Compound-53 | PA-15 | 1 | CA-8 | 3 | MA-5-2-2 | 4 |
| Compound-54 | PA-15 | 1 | CA-8 | 3 | MA-6-2-1 | 3 |
| Compound-55 | PA-15 | 1 | CA-8 | 2.6 | MA-15-2-4 | 3 |
| Compound-56 | PA-15 | 1 | CA-8 | 2.3 | MA-19-2-1 | 4 |
| Compound-57 | PA-15 | 1 | CA-9 | 3.5 | MA-1-2-1 | 4 |
| Compound-58 | PA-15 | 1 | CA-9 | 4 | MA-1-2-2 | 4 |
| Compound-59 | PA-15 | 1 | CA-9 | 3.1 | MA-5-2-1 | 3 |
| Compound-60 | PA-15 | 1 | CA-9 | 2.4 | MA-5-2-2 | 3 |
| Compound-61 | PA-15 | 1 | CA-9 | 2.4 | MA-6-2-1 | 3 |
| Compound-62 | PA-15 | 1 | CA-9 | 2.6 | MA-15-2-4 | 3 |
| Compound-63 | PA-15 | 1 | CA-11 | 2.5 | MA-1-2-2 | 4 |
| Compound-64 | PA-15 | 1 | CA-18 | 2.8 | MA-1-3-1 | 4 |
| Compound-65 | PA-15 | 1 | CA-20 | 2.5 | MA-6-2-1 | 3 |
| Compound-66 | PA-15 | 1 | CA-21 | 3 | MA-19-2-1 | 4 |

<Preparation of Lubricant>

The complex polyester composition shown in Table 1 and an organic metal compound were mixed into mineral oil (100 neutral oil, and viscosity at 100° C. of 4.4 mm/s$^2$) at ratios of conditions 1 to 5 shown in Table 2, and thus a lubricant was prepared. The friction coefficients of the lubricants of the conditions 1 to 5 were measured by the following method, and evaluation was performed on the basis of the following criteria. The results are shown in Table 3.

Furthermore, a light component in a GPC chart was calculated in the following conditions. A "HLC-8220GPC (manufactured by TOSOH CORPORATION) device" was used as a device, three columns of "TSKgel, SuperHZM-H (manufactured by TOSOH CORPORATION, 4.6 mmID×15 cm)", "TSKgel, SuperHZ4000 (manufactured by TOSOH CORPORATION, 4.6 mmID×15 cm)", and TSKgel, SuperHZ2000 (manufactured by TOSOH CORPORATION, 4.6 mmID×15 cm)" were used as a column, and "TSKguard-column, SuperHZ-H (manufactured by TOSOH CORPORATION, 4.6 mmID×15 cm)" was used as a guard column.

The conditions of GPC are as follows.
Eluant THF Stabilizer-Containing Liquid
Method THF8220
Flow Rate 0.35 ml/min
Measurement Temperature 40° C. (Column, Inlet, R.I.)
Analysis Time 20 minutes
Collection Conditions Sampling Pitch of 100 msec
Standard Concentration 0.1%
Sample Concentration 0.1% (5 mg+5 ml (Eluant) (Filtration with Filter of 0.45 μm)
Sample Injection Amount 10 μl
In addition, a calibration curve was prepared from the following six samples of "TSK standard POLYSTYRENE" manufactured by TOSOH CORPORATION.

$7.06 \times 10^5$ F-80(TS-201)
$1.90 \times 10^5$ F-20(TS-140)
$3.79 \times 10^4$ F-4(TS-202)
$1.81 \times 10^4$ F-2(TS-504)
$5.97 \times 10^3$ A-5000(TS-503)
$1.05 \times 10^3$ A-1000(TS-501)

<Evaluation>
(Friction Coefficient under Extreme Pressure Conditions)
The friction coefficient was measured by using a vibration-type friction abrasion test machine (manufactured by Optimol Instruments Prueftechnik GmbH, and product name: SRV 4) at a vibration frequency of 100 Hz, an amplitude of 2.0 mm, a load of 30 N, a temperature of 65° C., and a test time of 30 minutes.

A Rank: Friction Coefficient<0.050
B Rank: 0.050≤Friction Coefficient<0.055
C Rank: 0.055≤Friction Coefficient<0.060
D Rank: 0.060≤Friction Coefficient<0.070
E Rank: Friction Coefficient≥0.070

As known from Table 3, it is found that the friction coefficients of the lubricants of Examples 1 to 8 are suppressed to be extremely low. That is, the complex polyester composition obtained by the production method of present invention is able to exhibit excellent lubrication performance. In addition, in Examples 1 to 8, scale-up suitability is high, and thus the complex polyester composition is able to be mass produced.

In contrast, it is found that the friction coefficients of the lubricants of Comparative Examples 1 to 8 are large.

TABLE 2

| | | Condition 1 | Condition 2 | Condition 3 | Condition 4 | Condition 5 |
|---|---|---|---|---|---|---|
| Polyester Composition | Mass % | 1.00 | 1.00 | 1.00 | 1.00 | 1.00 |
| MoDTC | C8-MoDTC Amount of Mo (ppm) | — | — | 400 | — | 400 |
| | C16-MoDTC Amount of Mo (ppm) | — | — | — | 800 | — |
| ZnDTP | C3/C6 ZnDTP (Secondary) Amount of Phosphorus (Mass %) | — | — | — | — | 0.1 |
| Ashless Dispersant | Bron-Containing Succinic Acid Imide (Mass %) | — | 5 | 5 | 5 | 5 |

C8-MoDTC: Oxy Molybdenum Sulfide-N,N-Di-Octyl Dithiocarbamate
C16-MoDTC: Oxy Molybdenum Sulfide-N,N-Di-Tridecyl Dithiocarbamate
C3/C6 ZnDTP: Zinc Isopropyl-1-Ethyl Butyl Dithiophosphate

TABLE 3

| | Compound No. | GPC Area % of Component Having Weight Average Molecular Weight of Less than or Equal to 2000 | Friction Coefficient | | | | |
|---|---|---|---|---|---|---|---|
| | | | Condition 1 | Condition 2 | Condition 3 | Condition 4 | Condition 5 |
| Comparative Example 1 | Compound-10 | 48 | D | D | C | C | B |
| Comparative Example 2 | Compound-10 | 46 | B | B | B | B | B |
| Example 1 | Compound-10 | 43 | A | A | A | A | A |
| Example 2 | Compound-10 | 38 | A | A | A | A | A |
| Example 3 | Compound-10 | 34 | A | A | A | A | A |
| Comparative Example 3 | Compound-11 | 47 | C | C | C | C | C |
| Example 4 | Compound-11 | 33 | A | A | A | A | A |
| Comparative Example 4 | Compound-13 | 48 | D | D | C | C | C |
| Example 5 | Compound-13 | 38 | A | A | A | A | A |
| Comparative Example 5 | Compound-27 | 50 | D | D | C | C | C |
| Example 6 | Compound-27 | 40 | A | A | A | A | A |
| Comparative Example 6 | Compound-28 | 52 | D | D | C | C | C |
| Example 6 | Compound-28 | 43 | A | A | A | A | A |
| Comparative Example 7 | Compound-47 | 48 | C | C | B | B | B |
| Example 7 | Compound-47 | 37 | A | A | A | A | A |
| Comparative Example 8 | Compound-17 | 48 | D | D | C | B | C |
| Example 8 | Compound-17 | 40 | A | B | A | A | A |

Further, the same evaluation was performed by changing only the base oil as follows in the conditions 5 of Examples 1 to 3 and Comparative Examples 1 and 2. The results are shown in Table 4.

Base Oil A: (1) Distillate oil obtained by performing atmospheric pressure distillation with respect to paraffin-based crude oil and/or mix group-based crude oil Base Oil B: (2) Distillate oil (WVGO) obtained by performing reduced pressure distillation with respect to residual oil of atmospheric pressure residual oil of paraffin-based crude oil and/or mix group-based crude oil Base Oil C: (3) Synthetic wax (Fischer Tropsch wax, GTL wax, and the like) obtained by wax obtained from a lubricating oil dewaxing step (slack wax or the like) and/or gas to liquid (GTL) process or the like Base Oil D: (4) Mild hydrocracking treated oil of one type or two or more types of mixed oils and/or mixed oil selected from the base oils (1) to (3)

Base Oil E: (5) Two or more types of mixed oils selected from the base oils (1) to (4)

Base Oil F: (6) Deasphalted oil (DAO) of the base oil (1), (2), (3), (4), or (5)

Base Oil G: (7) Mild hydrocracking treated oil (MHC) of the base oil (6)

Base Oil H: (8) Two or more types of mixed oils selected from the base oils (1) to (7).

TABLE 4

|  | Compound No. | GPC Area % of Component Having Weight Average Molecular Weight of Less than or Equal to 2000 | Friction Coefficient (Condition 5) | | | | | | | |
|---|---|---|---|---|---|---|---|---|---|---|
|  |  |  | Base Oil A | Base Oil B | Base Oil C | Base Oil D | Base Oil E | Base Oil F | Base Oil G | Base Oil H |
| Comparative Example 1 | Compound-10 | 48 | D | C | C | C | C | D | C | C |
| Comparative Example 2 | Compound-10 | 46 | D | D | D | C | D | C | C | D |
| Example 1 | Compound-10 | 43 | A | B | A | B | A | B | A | B |
| Example 2 | Compound-10 | 40 | B | A | A | A | A | B | B | A |
| Example 3 | Compound-10 | 38 | A | A | B | A | B | A | A | A |

As known from Table 4, it is found that all of the friction coefficients of the lubricants of Examples 1 to 3 are suppressed to be low regardless of the type of base oil.

INDUSTRIAL APPLICABILITY

According to the present invention, it is possible to obtain a complex polyester composition which is able to exhibit excellent lubrication performance. Further, by using a production method of the present invention, it is possible to mass produce a complex polyester composition while reducing a load on an environment, and thus has high industrial applicability.

What is claimed is:

1. A production method for a complex polyester composition, comprising:
   obtaining a complex polyester composition by condensing polyhydric alcohol having three or more hydroxyl groups, a polycarboxylic acid having at least two carboxyl groups and carbon atoms of greater than or equal to 5, and monohydric alcohol having at least one oxyalkylene group in the absence of a solvent,
   wherein a component having a weight average molecular weight of less than or equal to 2000 in a GPC chart of the complex polyester composition is less than or equal to 43 area %.

2. The production method for a complex polyester composition according to claim 1, wherein the polyhydric alcohol is selected from pentaerythritol, trimethylol propane, glycerin, and dipentaerythritol.

3. The production method for a complex polyester composition according to claim 1, wherein the number of carbon atoms of the monohydric alcohol is greater than or equal to 6.

4. The production method for a complex polyester composition according to claim 1, wherein the monohydric alcohol is denoted by General Formula (1) described below, and

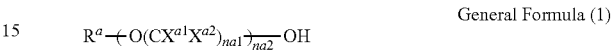

General Formula (1)

in General Formula (1), $R^a$ represents an alkyl group which may have a substituent group, a cycloalkyl group which may have a substituent group, an alkenyl group which may have a substituent group, an aryl group which may have a substituent group, or a heteroaryl group which may have a substituent group, $X^{a1}$ and $X^{a2}$ each independently represent a hydrogen atom, a halogen atom, or an alkyl group, na1 represents an integer of 2 to 4, and na2 represents an integer of 1 to 12.

5. The production method for a complex polyester composition according to claim 1, wherein the number of carbon atoms of the polycarboxylic acid is greater than or equal to 10.

6. The production method for a complex polyester composition according to claim 1, wherein the number of carbon atoms of the polycarboxylic acid is 24 to 48.

7. The production method for a complex polyester composition according to claim 1, wherein the polycarboxylic acid is a dimer acid or a trimer acid.

8. The production method for a complex polyester composition according to claim 1, wherein in obtaining the complex polyester composition, the polyhydric alcohol, the polycarboxylic acid, and the monohydric alcohol are condensed by being mixed such that an equivalence ratio of the polycarboxylic acid with respect to the polyhydric alcohol is 1 to 4, and an equivalence ratio of the monohydric alcohol with respect to the polyhydric alcohol is 0.5 to 5.

9. The production method for a complex polyester composition according to claim 1, wherein in obtaining the complex polyester composition, the polyhydric alcohol, the polycarboxylic acid, and the monohydric alcohol are condensed by being mixed such that an equivalence ratio of the polycarboxylic acid with respect to the polyhydric alcohol is 2.2 to 4, and an equivalence ratio of the monohydric alcohol with respect to the polyhydric alcohol is 2.5 to 5.

10. The production method for a complex polyester composition according to claim 1,
wherein the component having a weight average molecular weight of less than or equal to 2000 in a GPC chart is an ester component denoted by General Formula (2) described below, and

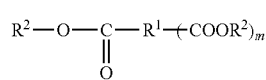

General Formula (2)

in General Formula (2), $R^1$ represents a (m+1)-valent or more chain or cyclic aliphatic linking group or an aromatic linking group, $R^2$ represents a group having an oxyalkylene structure, and m represents an integer of 1 to 3.

11. A complex polyester composition produced by the production method according to claim 1.

12. A lubricant composition containing the complex polyester composition according to claim 11, and at least one type of additives selected from an abrasion preventing agent, a viscosity index improver, an antioxidant, a cleaning agent, a dispersant, a fluidizing agent, a curing agent, a corrosion preventing agent, a seal compatible agent, a defoaming agent, a rust preventing agent, a friction adjuster, and a thickener.

13. A lubricant composition containing at least the complex polyester composition according to claim 11, and at least one type of mediums selected from mineral oil, a fatty oil compound, polyolefin oil, silicone oil, perfluoropolyether oil, diphenyl ether oil, aromatic ester oil, aliphatic monoester oil, aliphatic diester oil, and polyol ester lubricating oil.

14. A lubricant containing the complex polyester composition according to claim 11.

15. The lubricant according to claim 11,
wherein the lubricant is used as lubricating oil for grease, a releasing agent, engine oil for an internal combustion engine, oil for metal working or machining, oil for a bearing, fuel for a combustion engine, vehicle engine oil, gear oil, operating oil for an automobile, lubricating oil for a vessel and an aircraft, machine oil, turbine oil, hydraulic operating oil, compressor and vacuum pump oil, freezer oil, lubricating oil for metal working, a lubricant for magnetic recording medium, a lubricant for a micro machine, a lubricant for an artificial bone, shock absorber oil, or rolling oil.

* * * * *